US009128039B2

(12) United States Patent
Lee

(10) Patent No.: US 9,128,039 B2
(45) Date of Patent: Sep. 8, 2015

(54) BIOSENSOR TEST STRIP

(71) Applicant: Joinsoon Medical Technology Co., Ltd., Taipei County (TW)

(72) Inventor: Jen Fang Lee, Taipei County (TW)

(73) Assignee: Joinsoon Medical Technology Co., Ltd., New Taipei (TW)

( * ) Notice: Subject to any disclaimer, the term of this patent is extended or adjusted under 35 U.S.C. 154(b) by 435 days.

(21) Appl. No.: 13/645,211

(22) Filed: Oct. 4, 2012

(65) Prior Publication Data

US 2013/0087455 A1 Apr. 11, 2013

(30) Foreign Application Priority Data

Oct. 5, 2011 (TW) .............................. 100136061 A
Oct. 5, 2011 (TW) .............................. 100136062 A

(51) Int. Cl.
*G01N 27/327* (2006.01)
*G01N 33/487* (2006.01)

(52) U.S. Cl.
CPC ...... *G01N 27/3272* (2013.01); *G01N 33/48764* (2013.01); *G01N 33/48785* (2013.01)

(58) Field of Classification Search
CPC .................... G01N 27/3272; G01N 33/48764; G01N 33/4875; G01N 33/48785
See application file for complete search history.

(56) References Cited

U.S. PATENT DOCUMENTS

| 6,599,406 B1 * | 7/2003 | Kawanaka et al. ...... 204/403.02 |
| 2005/0100880 A1 | 5/2005 | Chang |
| 2011/0048972 A1 | 3/2011 | Moffat et al. |
| 2011/0144915 A1 | 6/2011 | Rodgers et al. |
| 2012/0111739 A1 * | 5/2012 | Pasqua et al. ............. 205/777.5 |

FOREIGN PATENT DOCUMENTS

| TW | 200523540 | 7/2005 |
| TW | 200944591 A | 11/2009 |
| TW | 201102647 A | 1/2011 |
| TW | I335428 | 1/2011 |

OTHER PUBLICATIONS

Google machine-generated English language translation of TW I335428, downloaded via the Taiwan Intelllectual Property Office on Feb. 06, 2015.*

Google machine-generated English language translation of TW 200523540, downloaded via the Taiwan Intelllectual Property Office on Feb. 06, 2015.*

(Continued)

*Primary Examiner* — Alexander Noguerola
(74) *Attorney, Agent, or Firm* — Novak Druce Connolly Bove + Quigg LLP

(57) ABSTRACT

This invention discloses a biosensor test strip that comprises a substrate, on which lies a conductive layer that contains a plurality of contact pads, check pads and reaction zones, which contains a plurality of working and reference electrodes, and on which the reaction reagent is deposited. The first contact pad is connected to the working electrode, while the second contact pad is connected to the reference electrode. Furthermore, this invention discloses a biosensor test strip for multiple tests on a single strip. The biosensor test strip includes a substrate with a plurality of incisions to divide the substrate into a plurality of individual test sections.

61 Claims, 24 Drawing Sheets

(56) References Cited

OTHER PUBLICATIONS

Google machine-generated English language translation of TW 200944591 A, downloaded via the Taiwan Intelllectual Property Office on Feb. 06, 2015.*

Google machine-generated English language translation of TW 201102647 A, downloaded via the Taiwan Intelllectual Property Office on Feb. 06, 2015.*

* cited by examiner

BIOSENSOR TEST STRIP

CROSS-REFERENCE TO RELATED APPLICATION

This application is based on and claims the benefits of priority from Taiwan Patent Application No. 100136061, filed on Oct. 5, 2011, and Taiwan Patent Application No. 100136062, filed on Oct. 5, 2011, the contents of which are incorporated by reference.

FIELD OF THE DISCLOSURE

The present invention relates to a biosensor test strip. More particularly, the present invention relates to a biosensor test strip with a sub-reference electrode and a sub-working electrode. Therefore, in a single test, more useful informations can be obtained to improve the accuracy of a blood glucose test.

Furthermore, the present invention relates to a biosensor test strip with a plurality of incisions and test sections, suitable to be used in a blood glucose test strip.

DESCRIPTION OF RELATED ART

Currently, a biosensor test strip for use in a blood glucose biosensor monitor, as shown in FIG. 1, has a substrate (10) and conductive tracks (92), which connect a working electrode (21) to a first contact pad (26) and a reference electrode (22) to a second contact pad (27). The contact pads have a first contact pad (26) and a second contact pad (27), and the reaction zone has a working electrode (21) and a reference electrode (22). Furthermore, the working electrode (21), the reference electrode (22) and an in-between zone form a reaction zone (20b) in which is deposited a reaction reagent. Thus, an electrochemical reaction occurs when an analyte reacts with the reaction reagent across the working electrode (21) and the reference electrode (22) under an applied electric potential. Electronic transfer between the working electrode (21) and the reference electrode (22) is proportional to the glucose concentration in the analyte. By measuring the electronic transfer under an applied electric potential between the working electrode (21) and the reference electrode (22), we can determine the glucose concentration in the analyte.

However, the above schematic drawing of a conventional biosensor test strip is a very basic one known for years. Based on the principle of electrochemical reaction, different biosensor test strips with more functions were developed. For example, Taiwan Patent No. 1335428 disclosed a test strip to determine if the amount of blood applied is sufficient for a successful electrochemical reaction between the working and reference electrodes. Nevertheless, none of the known patent applications or patents disclosed a design of test strip that is capable of simultaneously determining the blood glucose concentration, short fill of blood, as well as determining whether the applied analyte is a control solution or blood.

In addition, most of the currently available biosensor test strips are only for single use, which are too expensive for the poor people to test blood glucose, especially in poor countries, where proper management of diabetes is desperately needed to avoid further complications. In order to reduce the cost of testing with biosensor test strips, Taiwan Patent Application No. 097113766 entitled "BIOSENSOR TEST STRIPS FOR MULTIPLE TESTS ON A SINGLE STRIP" and Taiwan Patent Application No. 098122368 entitled "ELECTRO-CHEMICAL BIOSENSOR TEST STRIP" disclosed the design for a single biosensor test strip that can be used for multiple tests.

As shown in FIG. 2, Taiwan Patent Application No. 097113766 disclosed a biosensor test strip (59) with a plurality of test sections (20') separated by incision (57) and breaking indentations (51) at both sides to help break off the test section (20') after test. There is an air hole (58) to help sip in the applied analyte with capillary force. The biosensor test strip (59) consists of a plurality of test sections (20'), wherein a reference electrode (22) and a working electrode (21) are formed. One reaction zone (20b) is formed on each test section (20'), and a first contact pad (26) and a second contact pad (27) are on the farthermost end of the biosensor test strip (59). The first contact pad (26) and the second contact pad (27) are electrically connected to all the reaction zones (20b). When testing with the biosensor test strip, as shown in FIG. 3, the farthermost end of the biosensor test strip (59) is inserted into a biosensor monitor (80). The first and second contact pads (26, 27) can electrically transmit the generated electrical pulse current to the biosensor monitor (80). An analyte, such as a drop of blood, is applied to the test section (20') located on the other end of the biosensor test strip (59), opposite to the first contact pad (26) and a second contact pad (27). After the test, the biosensor test strip (59) is removed from the biosensor monitor (80). As shown in FIG. 4, the used test section (20') is then broken off from the other test sections (20') with the aid of incision (57) and the breaking indentations (51) at both sides. Unused test sections can be stored for further tests. The above design may reduce the cost of each measurement of blood glucose.

However, the above-mentioned structural design has the following disadvantages.

1. There is a serious concern that the user, such as the caregiver, may contaminate with the blood left on the used test section (20') when breaking off the used test section (20').

2. There is also a serious concern that the user, such as the caregiver, may contaminate with the blood left on the used test section (20') when removing the used biosensor test strip (59) from the biosensor monitor (80).

3. During the test on one test section (20'), the generated electric current not only passes through the test section (20'), but also passes through the other test sections (20') because the other test sections (20') will also expose to the environment with high humidity to make them conductive across the reference electrode (22) and the working electrode (21). As a result, the current measured by the biosensor monitor (80) will be lower than the actual current occurred on the test zone (20') where electrochemical reaction occurs to give wrong test result. The reaction reagents on the reaction zone (20b) of the unused test sections (20') will be slightly degraded after every repeated exposure to humidity in the environment. For example, assuming that there is a single biosensor test strip (59) with 10 test sections (20') to be tested for 10 times, however, the very last test section (20') will undertake 9 times of degradation before it is finally tested. Therefore, the blood glucose test results obtained from the last few test sections (20') could be inaccurate.

In view of the above drawbacks, the present invention studied, innovated and provided a biosensor test strip, which can be used to determine more than one parameter and which has a plurality of test sections.

SUMMARY OF THE INVENTION

The present invention aims to provide a biosensor test strip that includes a substrate, a conductive layer, a spacer layer, an adhesive layer and a cover layer. The conductive layer is formed on the substrate to have a number of contact pads, check pads, conductor tracks and a reaction zone. The spacer layer surrounds the reaction zone of the conductive layer rather than the contact pads of the conductive layer and has a flow path. The flow path passes through the reaction zone (i.e. through a sub-reference electrode, a working electrode, a reference electrode and a sub-working electrode). The adhesive layer covers the spacer layer without covering the contact pads of the conductive layer and has a recess corresponding to the flow path. The cover layer covers the adhesive layer without covering the contact pads of the conductive layer. In addition, the contact pads have a first contact pad and a second contact pad, and the reaction zone has a sub-reference electrode, a working electrode, a reference electrode and a sub-working electrode. Furthermore, the working electrode and sub-working electrode are connected to the first contact pad, and the reference electrode and sub-reference electrode are connected to the second contact pad. The sub-reference electrode, the working electrode, the reference electrode and the sub-working electrode are covered by a reaction reagent. at least one additional sub-reference electrode and at least one additional sub-working electrode. The sub-reference electrode is connected to the second contact pad and located in front of the reaction zone. Thus, a first electrical pulse current is obtained from the sub-reference electrode, which may define an initial time of first electrical pulse current when an analyte passes through the flow path on the biosensor test strip. The sub-working electrode is connected to the first contact pad and located behind the reaction zone. Thus, a second electrical pulse current is obtained once the analyte contacts the sub-working electrode. The time interval that the analyte flows through the reaction zone is therefore defined by the time difference between the first and second electrical pulse currents. Hence, the fluid velocity of the analyte is subsequently determined. With the fluid velocity known, the analyte may be determined to be either a control solution or blood based on the principle that the higher Hct (Hematocrit) content is, the slower the fluid velocity will be. Comparing with the data base stored in the meter, the Hct content of blood can be determined accordingly. Therefore, not only the type of the analytes but also electrical pulse currents can be obtained by the sub-reference electrode and the sub-working electrode which help determine the glucose concentration in the analyte. However, if the second electrical pulse current is not received, it will be an indication that that applied analyte is not sufficient for the measurement.

In a biosensor test strip disclosed in the present invention, a conductive layer can further contains a third contact pad, which is located in the zone with contact pads and is extended to form a sensor segment between the reference electrode and the sub-working electrode. A third electrical pulse is obtained once the analyte reaches the sensor segment and may be used to check whether a sufficient amount of analyte has been used. For example, if an electrical pulse current is obtained from the sensor segment, it means that the amount of analyte is sufficient. However, if no signal is obtained from the sensor segment, it means that the amount of analyte is not sufficient and the test might fail.

In a biosensor test strip disclosed in the present invention, a conductive layer can further contains a pair of check pads which electrically connects to the first contact pads, the working electrode and the sub-working electrode, or which electrically connects to the second contact pads, the reference electrode and the sub-reference electrode respectively. The check pads are used to determine if the electrical resistance across the working and reference electrodes are within the designated range, as a procedure of quality checks. If, however, the electrical resistance across the working and reference electrodes is out of the designated range, the biosensor test strip will be marked and removed.

Furthermore, in a biosensor test strip disclosed in the present invention, a spacer layer can be insulating glue, insulating paint, etc. and can be used to cover the conductive layer by printing. Alternatively, a cover layer can be used as a spacer layer and covers the conductive layer by a double sided adhesive layer or by high frequency induction heating. The flow path of the spacer layer contains a pair of aperture holes corresponding to the check pads, a flow path, a reaction chamber and a venting path. The flow path is extended from the front end of the spacer layer to the back and passes through the sub-reference electrode. The reaction chamber is located within the flow path to house the reaction reagent. The venting path is located at the end of the reaction chamber which passes through the sub-working electrode of the conductive layer. When an analyte (such as blood) is applied, the analyte enters the biosensor test strip from the flow path due to capillary force. Subsequently, an electrical pulse current upon contacting the sub-reference electrode is obtained. When the analyte enters the reaction chamber, the reaction reagent reacts with the analyte and an electrical pulse current is thus obtained from the reference electrode and the working electrode. When the analyte flows towards the venting path, the analyte contacts the sub-working electrode to provide another electrical pulse current.

The size of the above flow path near the venting path are far smaller than that of the reaction chamber.

In a biosensor test strip disclosed in the present invention, another a guiding path intersects with the flow path of the spacer layer and is located on the sub-reference electrode. After an analyte is applied to the test strip, the analyte flows through the front flow path and over the guiding path. After the analyte enters the reaction chamber, the electrical contact between sub-reference electrode and the working electrode can provide an electrical pulse current, which can be used to define the initial time when an analyte is just applied to the biosensor test strip.

In a biosensor test strip disclosed in the present invention, the size of the venting path of the spacer layer gets smaller as it approaches the outlet. Furthermore, the venting path travels over the sensor segment and the sub-working electrode. Since the size of the venting path can be about (but not limited to) 0.01-0.8 mm, an analyte with high viscosity (such as blood) cannot pass through easily and will be blocked by the venting path. However, if the analyte is a control solution, the analyte can successfully go through the sensor segment and contact the sub-working electrode due to its lower viscosity. Therefore, when an electrical pulse current is obtained from the sub-working electrode, such an electrical pulse current can be used to determine whether the analyte is a control solution or blood.

The end of the venting path of the spacer layer that is connected to an outer environment forms either a venting hole or air exit. In addition, the air exit may be located between the substrate and the adhesive layer. Therefore, the analyte can easily flow in the flow path. Moreover, the venting path of the present invention may connect to the venting hole or air exit, which passes through the cover layer and the adhesive layer, to form an air path for air to leave as blood is drawn in by capillary force.

The adhesive layer disclosed in the present invention may be a double sided adhesive layer, glue, etc. Alternatively, the adhesive layer may be attached to the cover layer, the spacer layer and the substrate by high frequency induction heating.

The cover layer disclosed in the present invention may be a hydrophilic PET plastic sheet, which helps the applied analyte flow under the cover layer by capillary force.

A biosensor test strip disclosed in the present invention includes a substrate, a conductive layer, a spacer layer, an adhesive layer, a cover layer, with a plurality of incisions formed between the test sections on the substrate. The conductive layer is formed on the substrate with a plurality of test sections. Each of the test sections includes contact pads, check pads, and a reaction zone. The spacer layer surrounds reaction zone of each test section of the conductive layer rather than the contact pads. The spacer layer further has a pair of aperture holes corresponding to the check pads and a plurality of flow path. Each of the flow path passes through the front flow path, the reaction zone, and the venting path. The adhesive layer covers the spacer layer without covering the contact pads of the conductive layer, which has a recess corresponding to the flow path. There is another cover layer to cover the adhesive layer without covering the contact pads of the conductive layer, but leaving a pair of aperture holes corresponding to the check pads. Besides, each test section separated by two incisions forms a small piece of biosensor test strip which can be independently tested on a biosensor monitor. In addition, the contact pads has a first contact pad and a second contact pad, each of which connects to the working electrode and the reference electrode respectively. To be more specific, the working electrode is connected to the first contact pad and the reference electrode is connected to the second contact pad. The working electrode, the reference electrode and an in-between zone form a reaction zone to be covered with a reaction reagent. Moreover, the reaction zone further may have at least one additional sub-reference electrode and at least one additional sub-working electrode. The sub-reference electrode is connected to the second contact pad and is located in front of the reaction zone. Thus, a first electrical pulse current is obtained between the sub-reference electrode and working electrode to define the initial time of first electrical pulse current when an analyte passes through the flow path on the biosensor test strip. The sub-working electrode is connected to the first contact pad and is located behind the reaction zone. Thus, a second electrical pulse current can be obtained between the sub-working electrode and the reference electrode. The time interval that the analyte flows through the flow path over reaction zone is therefore defined as the time difference between the first and second electrical pulse currents which is related to the fluid velocity and hence viscosity or type of the analyte to be subsequently determined. However, if the second electrical pulse current is not received, it will be an indication that that applied analyte is not sufficient for the measurement.

The test sections of the above conductive layer can be so arranged that the first contact pads of all the test sections are electrically connected to each other. After a conductive layer is formed on a substrate, the substrate is immersed under conductive chemical solutions, in which the conductive layer is connected to a positive electrode (or a negative electrode) and the conductive chemical solutions are connected to the other electrode. After an electric potential is applied, impurities on the conductive layer can be removed by electrolysis. That is, the residual impurities or oxidants on the conductive tracks, working and reference electrodes, and contact pads of the conductive layer can be removed by oxidation or reduction process. As a result, the stability of the biosensor test strip is enhanced. After the above process, a spacer layer, an adhesive layer, a cover layer with incisions can be subsequently attached onto.

In a biosensor test strip disclosed in the present invention, a working electrode is connected to a first contact pad and a reference electrode is connected to a second contact pad. In addition, check pads with bigger areas are closer to the working electrode and the reference electrode to reduce redundant electrical resistance which might distort the accuracy of measurement on the check pads. During the manufacture of the biosensor test strip, quality control can be made by applying an electric potential over the check pads on which reaction reagent stays, to determine if the electrical resistance of the reaction reagent over the working electrode and reference electrode is within the designated range or not. Moreover, the distance between the check pads and the working electrode, as well as between the check pads and the reference electrode can be smaller than, but not limited to, 5 mm in order to enhance the accuracy of measurement on check pads.

A biosensor test strip disclosed in the present invention includes a substrate, a conductive layer, a spacer layer, an adhesive layer, a cover layer with a plurality of incisions formed between test sections. The conductive layer is formed on the substrate to have contact pads, a pair of check pads, and a plurality of test sections connected in series. The spacer layer surrounds the reaction zones of the conductive layer rather than the contact pads of the conductive layer with a plurality of flow path, but leaving a pair of aperture holes corresponding to the check pads. Each of the flow paths passes through the font flow path, the reaction zone, and the venting path. The adhesive layer covers the spacer layer without covering the contact pads of the conductive layer and has a pair of aperture holes corresponding to the check pads, and a recess corresponding to each of the flow paths. The cover layer covers the adhesive layer without covering the contact pads of the conductive layer, also having a pair of aperture holes corresponding to the check pads. In addition, the contact pads have a first contact pad and a second contact pad. Each reaction zone has a working electrode and a reference electrode. Therefore, the biosensor test strip of the present invention can be used for more than one test on a single test strip. Furthermore, the working electrode is connected to the first contact pad and the reference electrode is connected to the second contact pad. The working electrode, the reference electrode and an in-between zone form a reaction zone to be covered by a reaction reagent. Moreover, each reaction zone houses at least one additional sub-reference electrode and at least one additional sub-working electrode. The sub-reference electrode is connected to the second contact pad and is located in front of each reaction zone. Thus, a first electrical pulse current is obtained when the analyte contacts across the sub-reference electrode and the working electrode, which may define an initial time of first electrical pulse current when an analyte passes through the flow path on the biosensor test strip. The sub-working electrode is connected to the first contact pad and is located in a rear end of each reaction zone. Thus, a second electrical pulse current is obtained from the sub-working electrode and the reference electrode. The time interval that the analyte flows through the reaction zone is therefore defined by the time difference between the first and second electrical pulse currents. Hence, the fluid velocity of the analyte is subsequently determined. With the fluid velocity known, the analyte may be determined to be either a control solution or blood based on the principle that the higher viscosity is, the slower the fluid velocity will be. The Hct content of blood can be determined subsequently.

In each reaction zone of the above embodiment, a working electrode is connected to a first contact pad and a reference electrode is connected to a second contact pad. In addition, check pads with bigger areas are closer to the working electrode and the reference electrode. During the manufacture of the biosensor test strip, quality control can be done by applying an electric potential across the working electrode and the reference electrode with the reaction reagent solution deposited thereonto, to determine if the electrical resistance of the reaction reagent is within the designated range or not.

In the biosensor test strip disclosed in the present invention, the incision can be a slot, an indent, a through groove etc. formed by stamping or other means. The incisions can go through the cover layer, the adhesive layer, the spacer layer and a part of the substrate. Alternatively, the incisions may only be formed on the cover layer. By applying stress on the incisions, a test section of the biosensor test strip can be obtained. The shape of the incisions and the process of forming the incisions are not limited.

The present invention aims to provide a biosensor test strip with a plurality of incisions and test sections that includes a substrate with a plurality of incisions and a plurality of conductive layers on the test sections. The plurality of incisions can divide the substrate into a plurality of test sections. Each test section has a first side and a second side. The first side is defined as the side away from a biosensor monitor when inserting into the biosensor monitor. The second side is defined as the side close to the biosensor monitor when inserting into the biosensor monitor. Furthermore, each test section includes an independent first and second contact pads, check pads and reaction zones. The reaction zone is located on the first side of the test section. The first and second contact pads are electrically connected to the reaction zone and the check pads which are located on the second side of the test section. Therefore, when the first test section of the biosensor test strip is inserted into a biosensor monitor and is removed from the other test sections by applying a bending force on the incision, the remaining other test sections are securely stored in a vial for further tests. After the test is finished, the used test section is ejected from the biosensor monitor by the eject mechanism on the biosensor monitor to avoid contact with the analyte.

In a biosensor test strip with a plurality of incisions and test sections disclosed in the present invention, each reaction zone includes at least one working electrode and one reference electrode. The working electrode, the reference electrode and an in-between zone form a reaction zone to be covered by a reaction reagent. In addition, the working electrode is connected to a first contact pad and the reference electrode is connected to a second contact pad.

In a biosensor test strip with a plurality of incisions and test sections disclosed in the present invention, a first contact pad is connected to at least one additional sub-working electrode and a second contact pad is connected to at least one additional sub-reference electrode. A combination of several electrical pulse currents can be obtained from the sub-reference electrode, the working electrode, the reference electrode and the sub-working electrode once an analyte enters the test section to react with the reaction reagent on the reaction zone. An initial time when the analyte is applied to the biosensor test strip can thus be easily defined. It can also be noted when the analyte leaves the reaction zone, it contacts with the reference electrode and the sub-working electrode to give another electrical pulse current. Thus, the time interval between the first and the second electrical pulse current is the time that the analyte takes to flow through the reaction zone, which is used to determine if the applied analyte is control solution or blood with Hct content. The present invention does not limit the number and shape of the sub-working electrode and also does not limit the number and shape of the sub-reference electrode.

In a biosensor test strip with a plurality of incisions test sections disclosed in the present invention, there are check pads connecting to the working electrode and reference electrode respectively to determine if the electrical resistance of the reaction reagent over the working and reference electrodes under an applied electric potential is within the designated range or not during the manufacture of the biosensor test strip. If the electrical resistance between the contact pads across the working and reference electrodes are out of the designated range, the tested biosensor test strip will be marked and removed.

In a biosensor test strip with a plurality of incisions test sections disclosed in the present invention, conductive layers are so arranged such that first contact pads are electrically connected to each other and second contact pads are electrically connected to each other. After the conductive layers are formed on a substrate, the substrate is immersed in a conductive chemical solution. Afterwards, the conductive layer is connected to a positive electrode (or a negative electrode) and the conductive chemical solutions are connected to the other electrode. After an electric potential is applied, the residual impurities or oxidants on the conductive layers can be removed by oxidation or reduction process. As a result, the stability of the biosensor test strip is thereby enhanced. After the above process, a spacer layer, a hydrophilic layer, a cover layer with incisions can be subsequently attached onto.

In a biosensor test strip with a plurality of incisions and test sections disclosed in the present invention, the main feature is that a biosensor test strip is so designed to have a plurality of test sections by a plurality of incisions. Moreover, each test section has its own conductive layer and the conductive layer has a reaction zone, check pads, and a first contact pad and a second contact pad to connect to a biosensor monitor. Therefore, the first test section of the biosensor test strip disclosed in the present invention can be inserted into the biosensor monitor and broken off to leave in the biosensor monitor for test, with the other test sections safely stored in the vial for further tests. As an analyte (such as blood) enters the biosensor test strip from the first side of the test section, it travels across the font flow path, the reaction zone and then venting path to give a series of various electrical current. After the test, the used test section in the biosensor monitor can be ejected by an eject mechanism in the biosensor monitor. As a result, during the eject process of the used test section, the test section with the analyte will not contact the user or the caregiver to avoid blood contamination.

Every time the biosensor test strip with a plurality of incisions test sections disclosed in the present invention is tested, only one test section is left in the biosensor monitor. The other test sections, which are safely stored in the vial, will not be degraded by repeated exposure to humidity in the environment or applied electric potential. The accuracy of each test can therefore be enhanced.

DETAILED DESCRIPTION OF THE INVENTION

Figure 1:
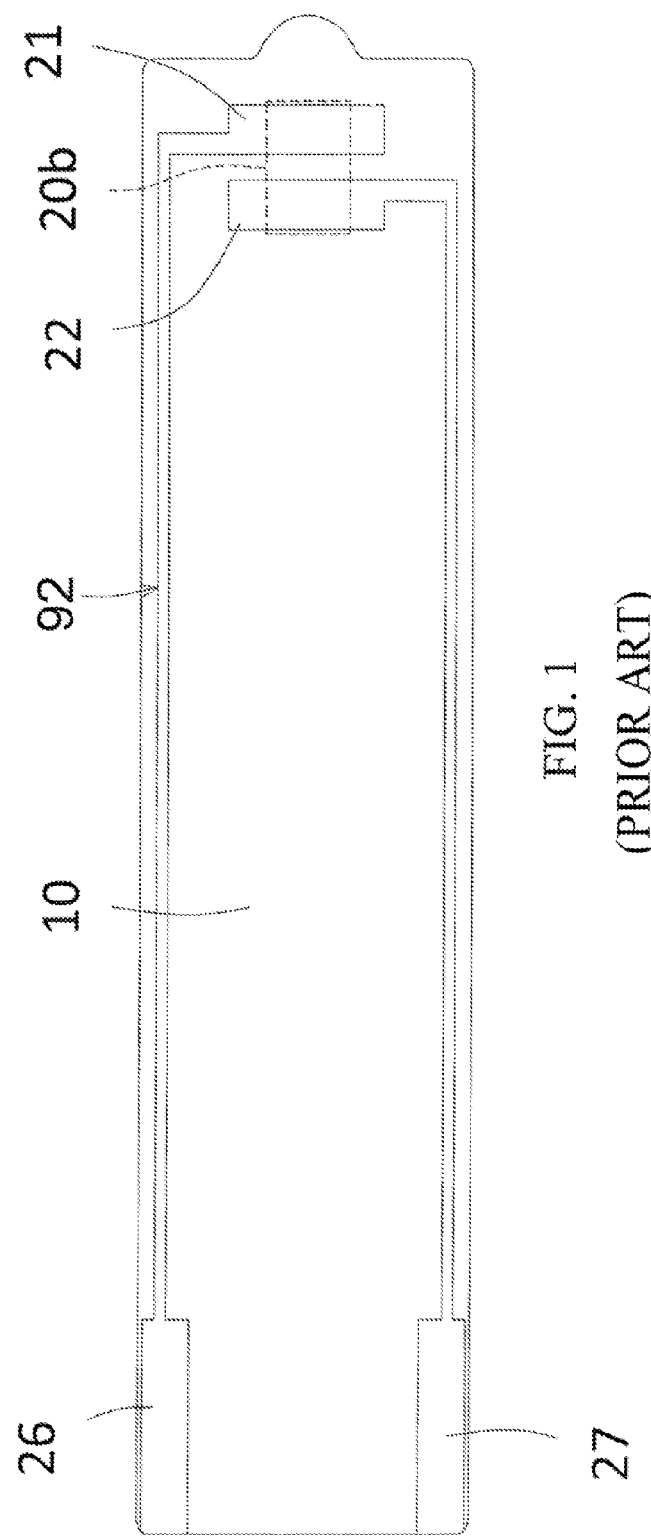
FIG. 1 shows a schematic drawing of a conventional biosensor test strip.
Figure 2:
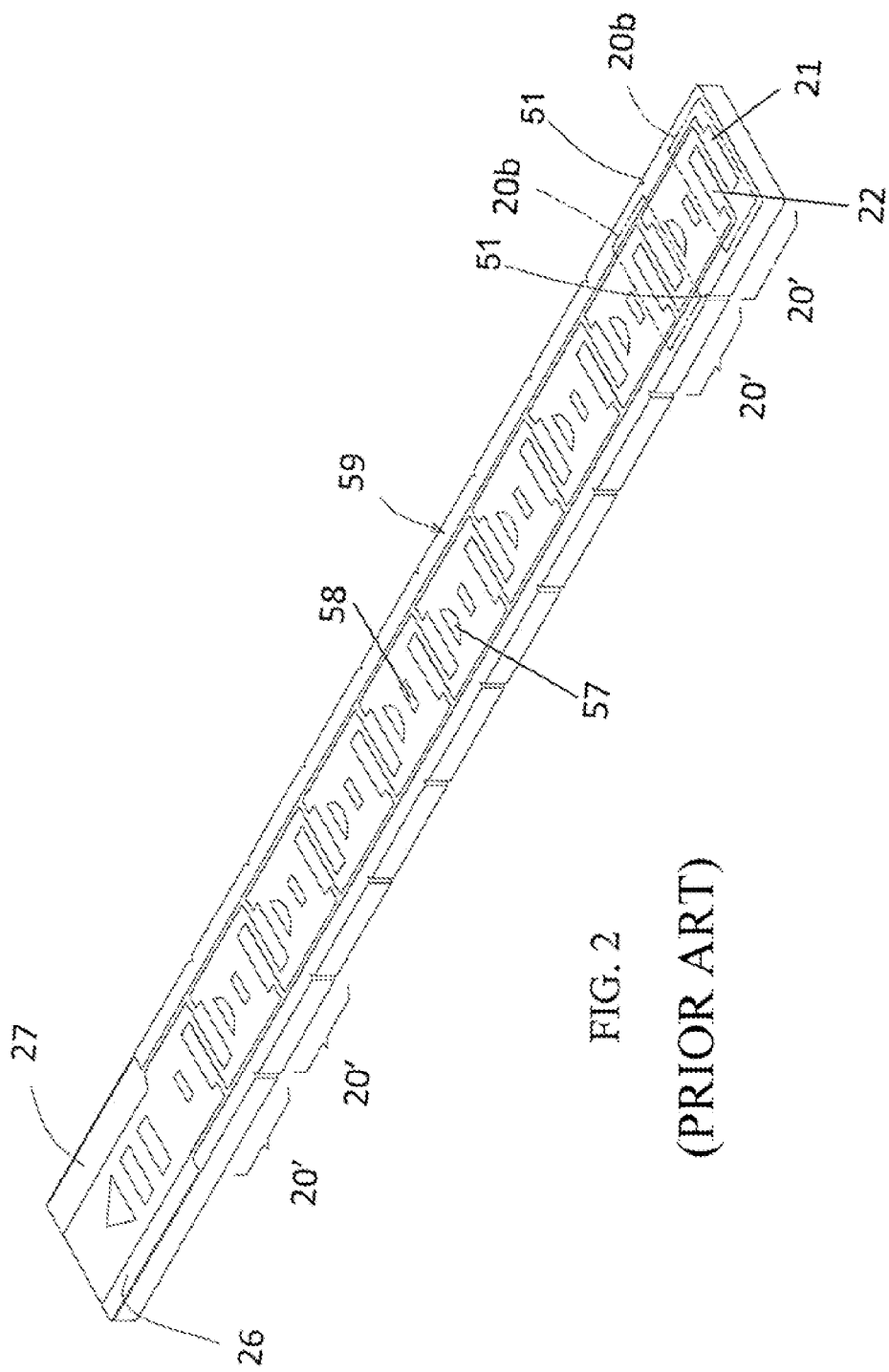
FIG. 2 shows a 3D drawing of a conventional biosensor test strip with a plurality of test sections.
Figure 3:
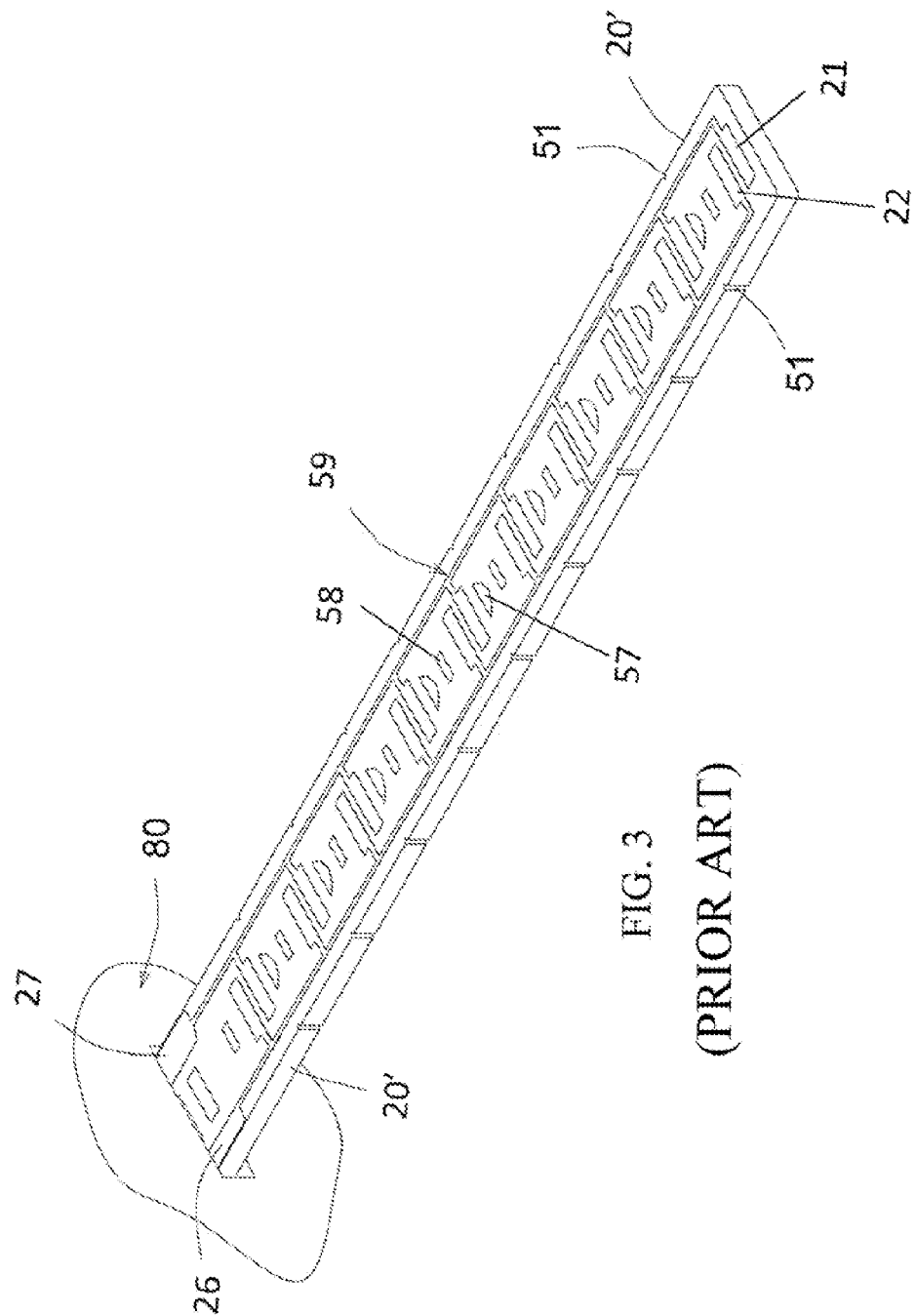
FIG. 3 shows the design of the a conventional biosensor test strip with a plurality of test sections.
Figure 4:
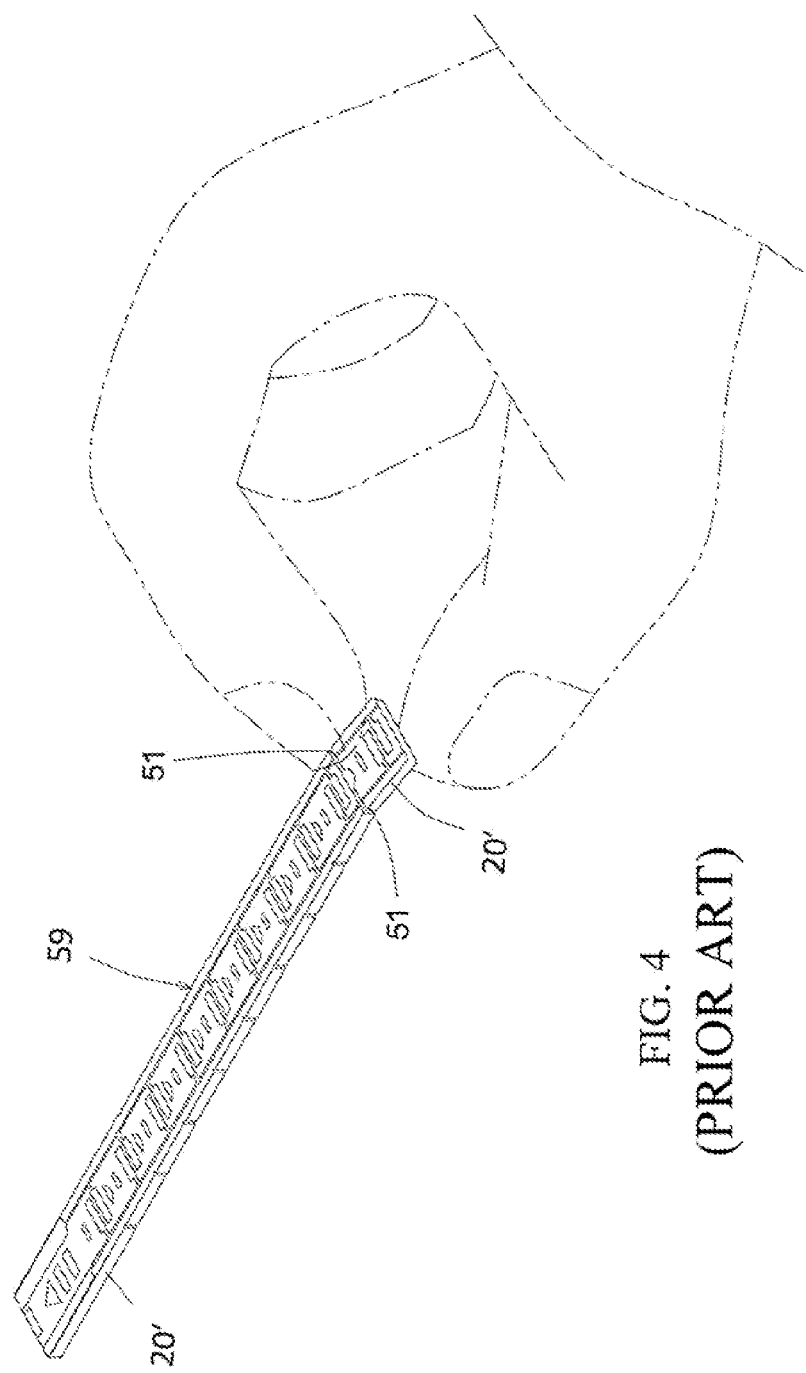
FIG. 4 shows the conventional biosensor test strip with a plurality of test sections (20') after testing.

The following illustrative embodiments are provided to illustrate the disclosure of the present invention. These and other advantages and effects of the present invention can be apparently understood by those skilled in the art after reading the disclosure of this specification.

Referring to FIGS. 5-20, the present invention relates to a biosensor test strip (59) that includes a substrate (10), a conductive layer (20), a spacer layer (30), an adhesive layer (40) and a cover layer (50). The conductive layer (20) at least contains contact pads (20a), check pads (211), and at least one reaction zone (20b). The reaction zone (20b) contains a working electrode (21) and a reference electrode (22). The working electrode (21), the reference electrode (22) and an in-between zone form a reaction zone (20b) where reaction reagent applies. Furthermore, in the reaction zone (20b), at least one additional sub-reference electrode (24) and at least one additional sub-working electrode (25) may be contained. The time needed for an analyte to flow through the reaction zone (20b) will give the fluid velocity of an analyte from the electronic signals generated between the sub-reference electrode (24), the working electrode (21), the reference electrode (22) and the sub-working electrode (25). The fluid velocity may further give results relating to control solution, or blood with Hct (Hamatocrit) content. However, if the second electrical pulse current is not received, it will be an indication that that applied analyte is not sufficient for the measurement.

The above reaction reagent is an enzyme reagent which may contain ingredients of, but not limited to, hydroxypropyl methylcellulose, citric acid, dipotassium phosphate, nonionic surfactant, glucose oxidase (or glucose dehydrogenase), potassium ferricyanide, dH2O and carbon nanotube, etc. However, the present invention is not limited to the above ingredients.

As shown in FIGS. 5-9, a biosensor test strip (59) disclosed in the present invention includes a substrate (10), a conductive layer (20), a spacer layer (30), an adhesive layer (40), and a cover layer (50). The conductive layer (20) is formed on the substrate (10) to contain contact pads (20a), check pads (211) and a reaction zone (20b). The spacer layer (30) surrounds the reaction zone (20b) of the conductive layer (20) rather than the contact pads (20a) of the conductive layer (20), to have a pair of aperture holes (38) corresponding to the check pads (211) and has a flow path (31). The flow path (31) passes through the reaction zone (20b) (i.e. through a sub-reference electrode (24), a working electrode (21), a reference electrode (22) and a sub-working electrode (25). In addition, the spacer layer may contain a pair of aperture holes (38) which corresponds to the check pads (211) on the conductive layer (20). The adhesive layer (40) covers the spacer layer (30) without covering the contact pads (20a) of the conductive layer (20) and has a recess (41) to accommodate reaction reagent to flow in which corresponds to the flow path (31). The adhesive layer (40) may also contain a pair of aperture holes (38) which corresponds to the check pads (211) on the conductive layer (20). The cover layer (50) covers the adhesive layer (40) without covering the contact pads (20a) of the conductive layer (20). The cover layer (50) further has a pair of aperture holes (38) which corresponds to the check pads (211) on the conductive layer (20). Please note that the contact pads (20a) has a first contact pad (26) and a second contact pad (27). The reaction zone (20b) accommodates a working electrode (21) and a reference electrode (22). Furthermore, the working electrode (21) is connected to the first contact pad (26) and the reference electrode (22) is connected to the second contact pad (27). The working electrode (21), the reference electrode (22) and an in-between zone reaction reagent form a reaction zone (20b) where reaction reagent applies. Moreover, the reaction zone (20b) may further contain at least one additional sub-reference electrode (24) and at least one additional sub-working electrode (25). The sub-reference electrode (24) is connected to the second contact pad (27) and is located in front of the reaction zone (20b). Thus, when an analyte passes through the flow path (31) on biosensor test strip (59), a first electrical pulse current is obtained between the sub-reference electrode (24) and working electrode (21). The sub-working electrode (25) is connected to the first contact pad (26) and is located inside the reaction zone (20b). Thus, a second electrical pulse current can be obtained between the sub-working electrode (25) and the reference electrode (22). With the first and second electrical pulse currents measured, the time interval needed for the analyte to flow through the reaction zone (20b) is determined. Based on the time interval, the fluid velocity of the analyte is obtained and is used to determine the viscosity of the analyte, and hence, control solution from blood with Hct content. Therefore, in addition to the electrical response obtained from the electrochemical reaction occurred on the reaction zone (20b), more informations can be obtained from between the sub-reference electrode (24), working electrode (21), reference electrode (22) and the sub-working electrode (25), such as type of the analyte to be further determined.

Figure 10:
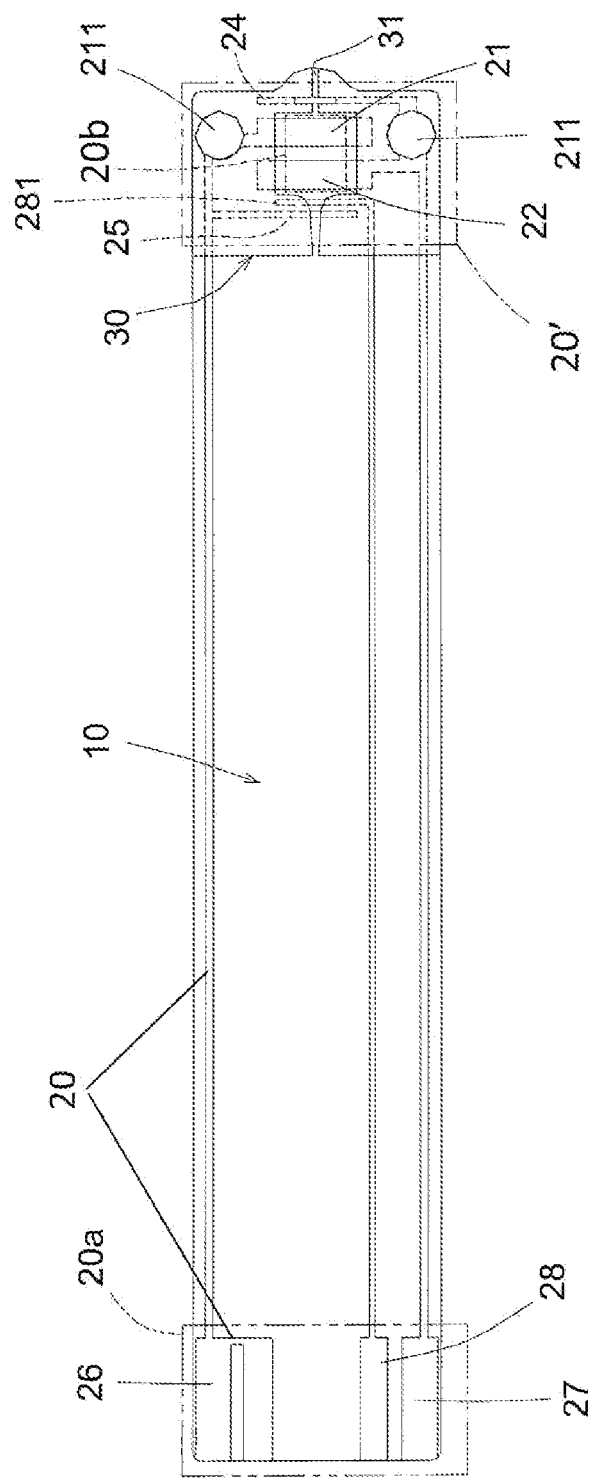
FIG. 10 shows a 2D schematic drawing of the second embodiment of the present invention.
Figure 11:
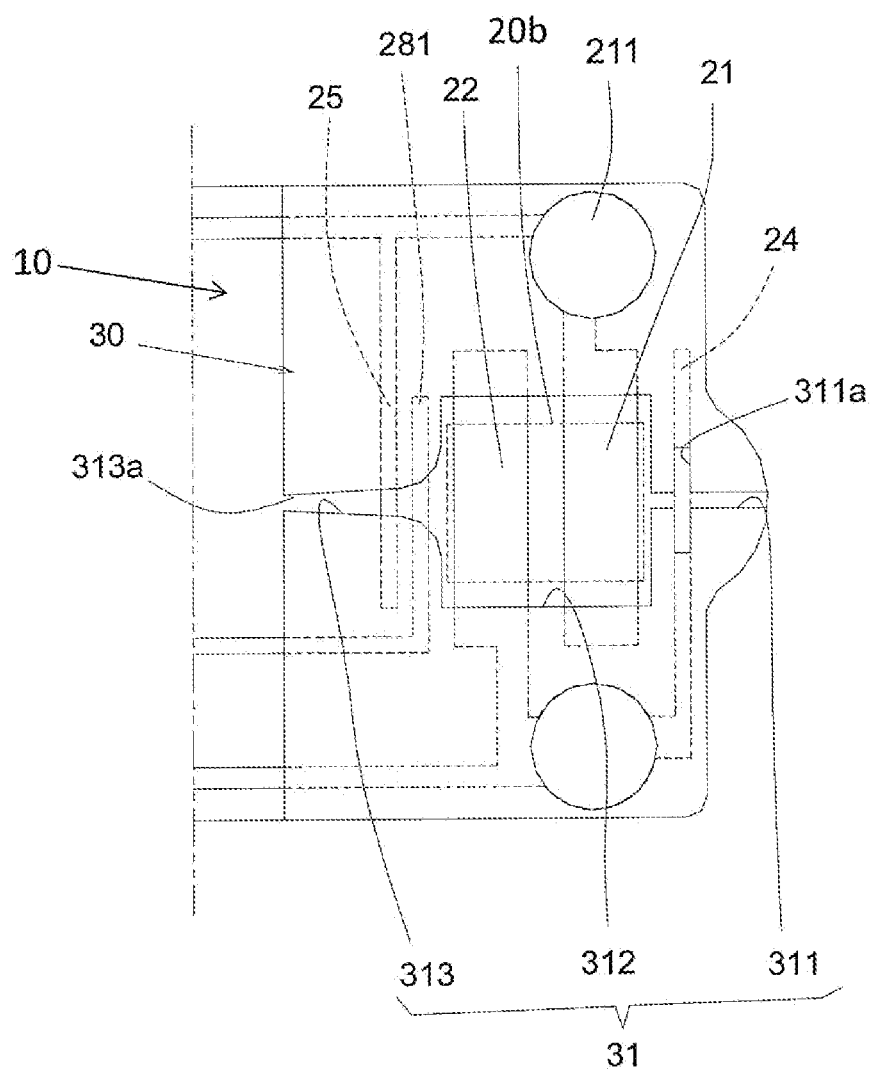
FIG. 11 shows a partially enlarged view of FIG. 10.
Figure 12:
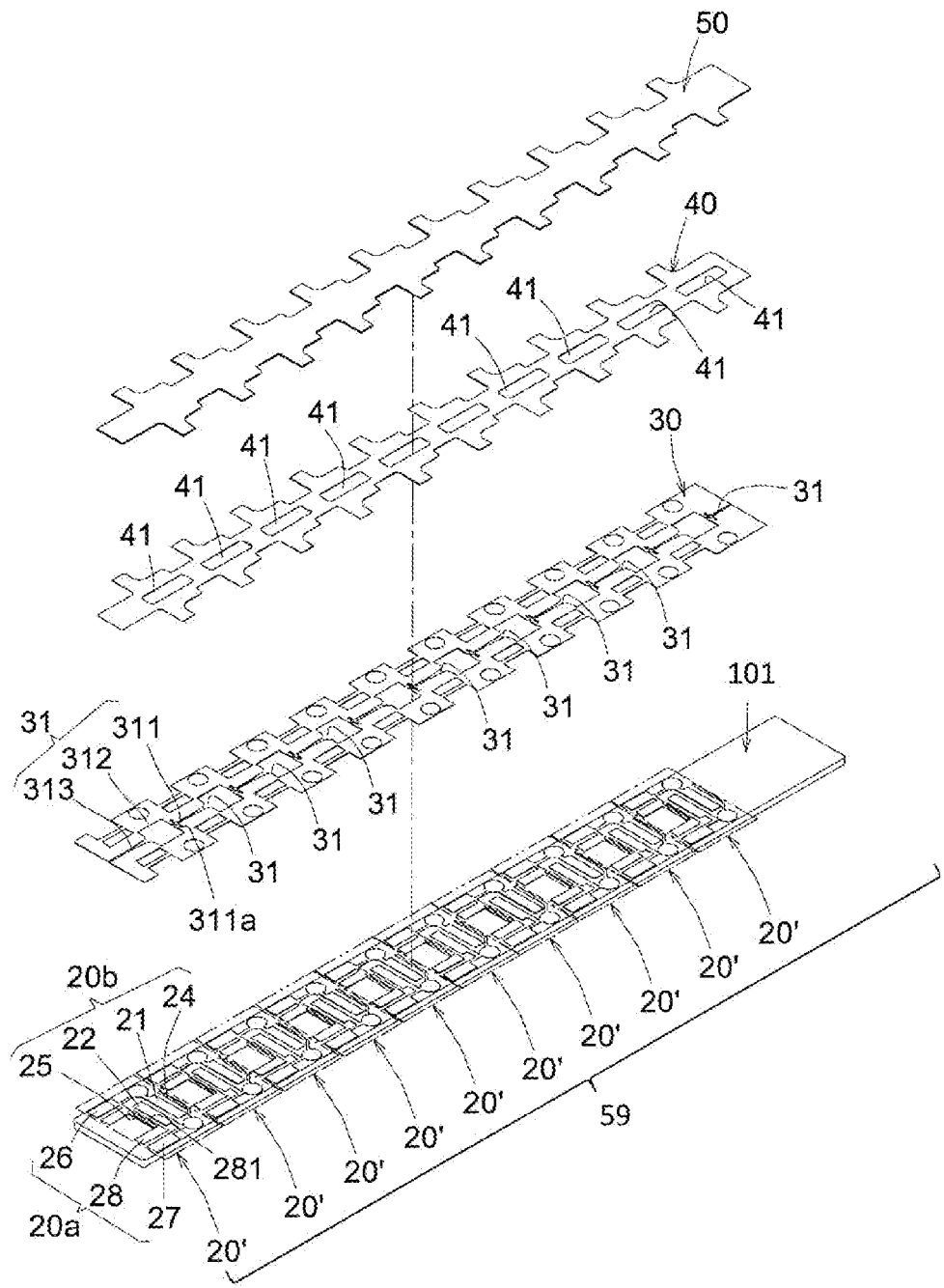
FIG. 12 shows an exploded view of the third embodiment of the present invention.
Figure 13:
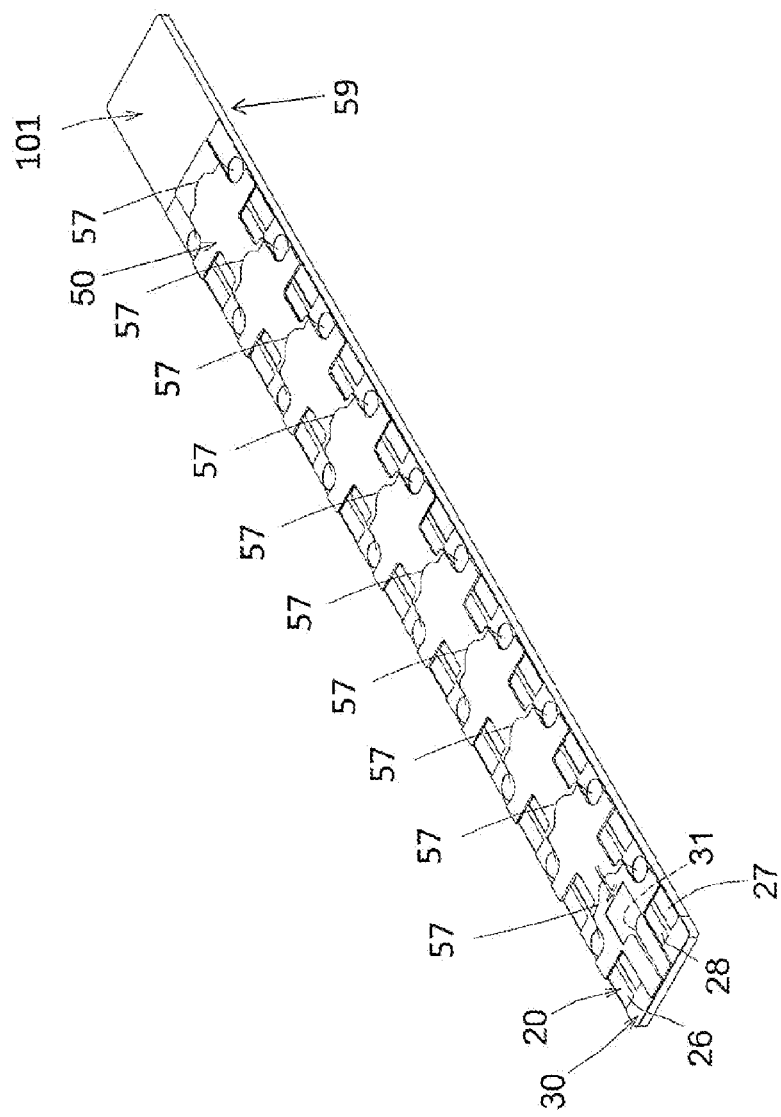
FIG. 13 shows a 3D schematic drawing of the embodiment shown in FIG. 12.
Figure 14:
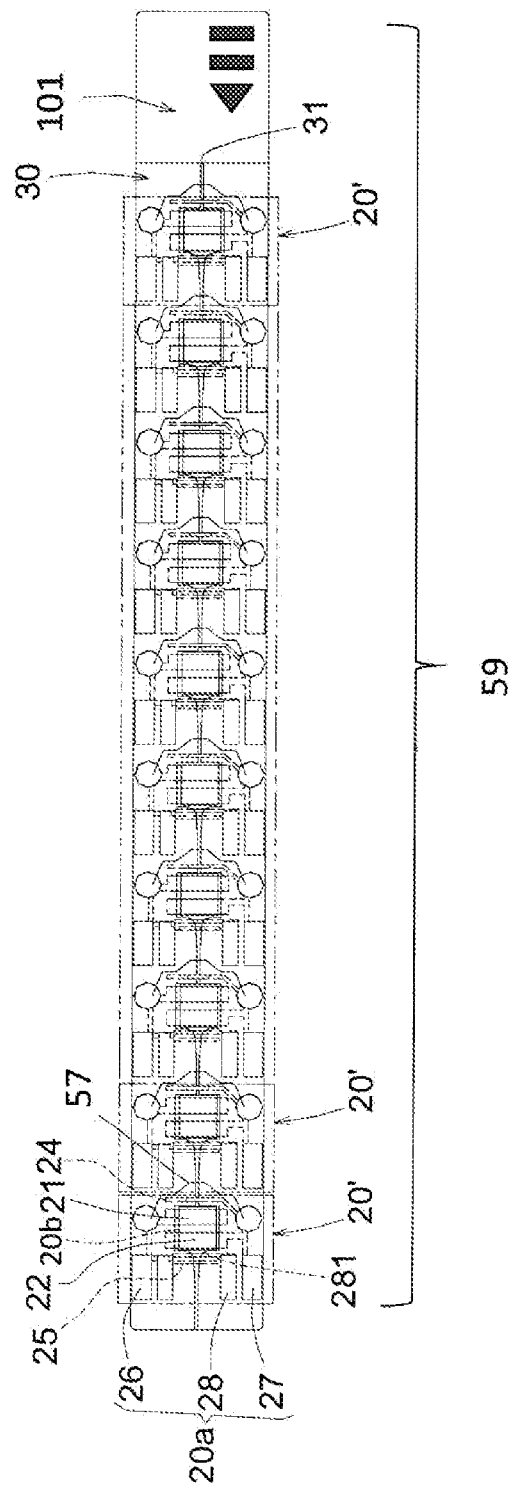
FIG. 14 shows a 2D schematic drawing of FIG. 12.
Figure 15:
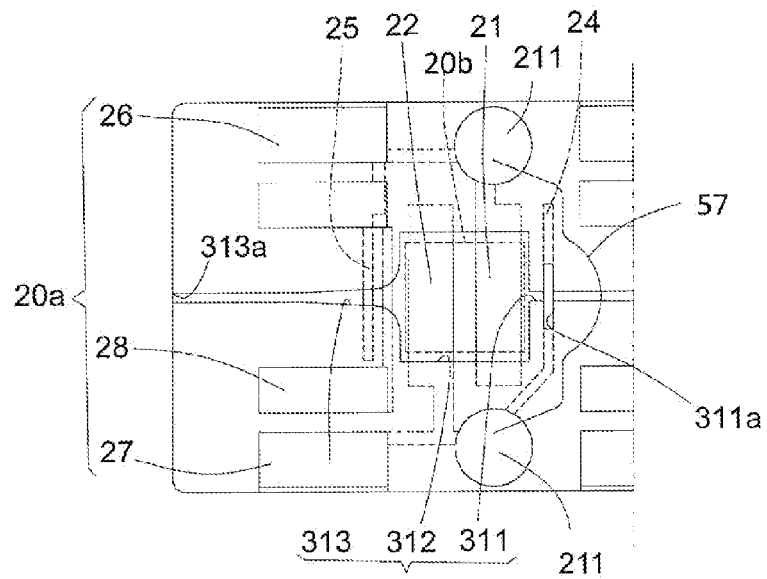
FIG. 15 shows a partially enlarged view of FIG. 14.

As shown in FIGS. 10-11, in a biosensor test strip (59) disclosed by the preferred embodiment of the present invention, a conductive layer (20) can further contains a third contact pad (28), which is further extended to electrically connect to the sensor segment (281) in the reaction zone (20b), located between the reference electrode (22) and the sub-working electrode (25). A third electrical pulse current may be obtained as the analyte reaches the sensor segment (281), which may be used to check if sufficient amount of analyte has been tested. For example, if a third electrical pulse current is obtained from the sensor segment (281), it means that the amount of analyte is sufficient. But, if no signal is obtained from the sensor segment (281), it means that the amount of analyte is not sufficient and the test fails. Alternatively, based on the electrical pulse current generated from the sub-reference electrode (24) and working electrode (21), as well as the electrical pulse current generated from the sub-working electrode (25) and reference electrode (22), the fluid velocity of the analyte can be obtained and be used to determine whether the analyte is a control solution or blood with Hct content.

Furthermore, in a biosensor test strip (59) disclosed in the present invention, a spacer layer (30) can be insulating glue, insulating paint, etc. and can be used to cover the conductive layer (20). Alternatively, a cover layer can be used as a spacer layer (30) to cover the conductive layer (20) by a double sided adhesive layer or high frequency induction heating. As shown in FIG. 11, the flow path (31) of the spacer layer (30) contains a front flow path (311), a reaction chamber (312) and a venting path (313). The front flow path (311) extends from the front end of the biosensor test strip (59) to the rear end of the spacer layer (30) through the sub-reference electrode (24) and sub-working electrode (25). The reaction chamber (312) is located at the end of the front flow path (311). The venting path (313) is located at the end of the reaction chamber (312) and passes through the sub-working electrode (25) of the conductive layer (20). The reaction chamber (312) corresponds to the reaction zone (20b). When an analyte (such as blood) is applied, the analyte enters the biosensor test strip from the front flow path (311) due to capillary force. An electrical pulse current is formed when the analyte contacts across the sub-reference electrode (24) and working electrode (21). When the analyte enters the reaction chamber (312), the reaction reagent reacts with the applied analyte under an applied electric potential. Furthermore, as the analyte flows towards the venting path (313), the analyte contacts across the sub-working electrode (25) and reference electrode (22) to give another electrical pulse current. Please note that the size of the front flow path (311) and the venting path (313) are much smaller than that of the reaction chamber (312). In a biosensor test strip (59) disclosed in the present invention, a guiding path (311a) intersects with the front flow path (311) of the spacer layer (30) and is located over the sub-reference electrode (24). After an analyte is applied to the biosensor test strip, the analyte enters the front flow path (311) through the recess (41) over the guiding path (311a), which makes larger contact with the analyte. Before the analyte enters the reaction chamber (312), the sub-reference electrode (24) and the working electrode (21) can be electrically connected to provide an electrical pulse current, which can be used to define an initial time when an analyte is applied to the biosensor test strip (59).

Figure 19:
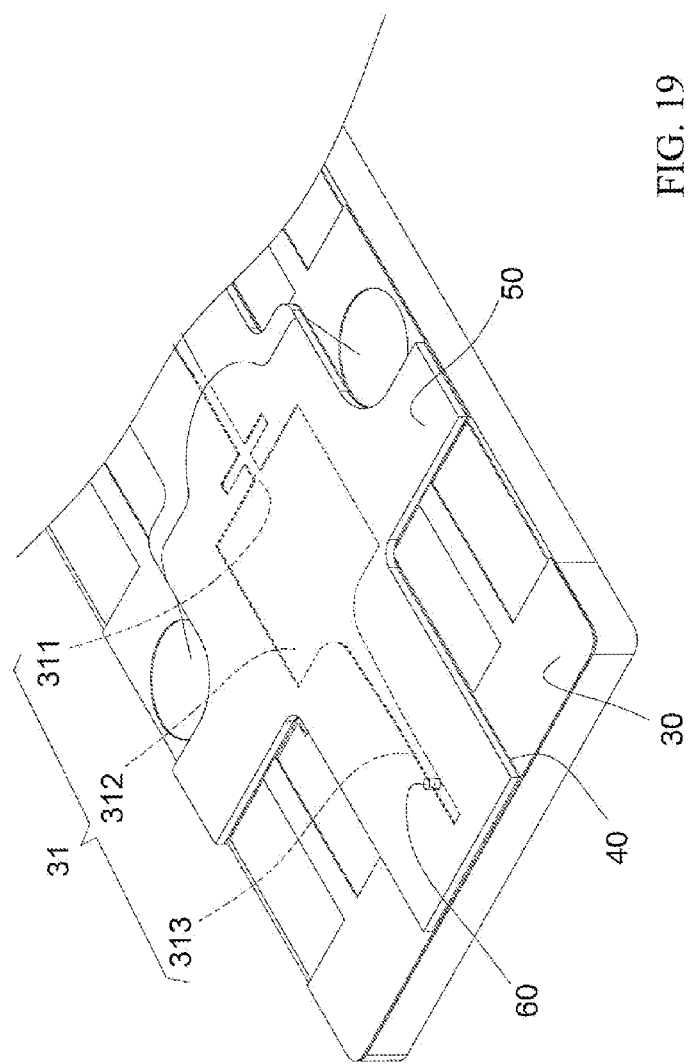
FIG. 19 shows a 3D schematic drawing of the sixth embodiment of the present invention.
Figure 20:
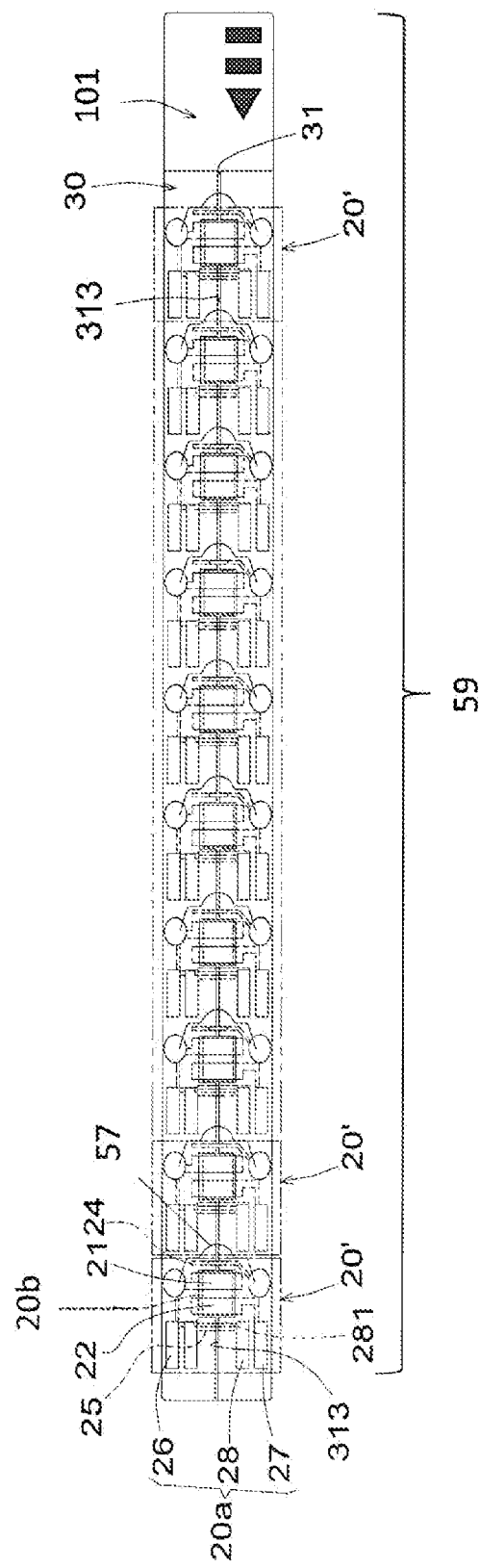
FIG. 20 shows a schematic drawing for another example of the spacer layer of the present invention.
Figure 21:
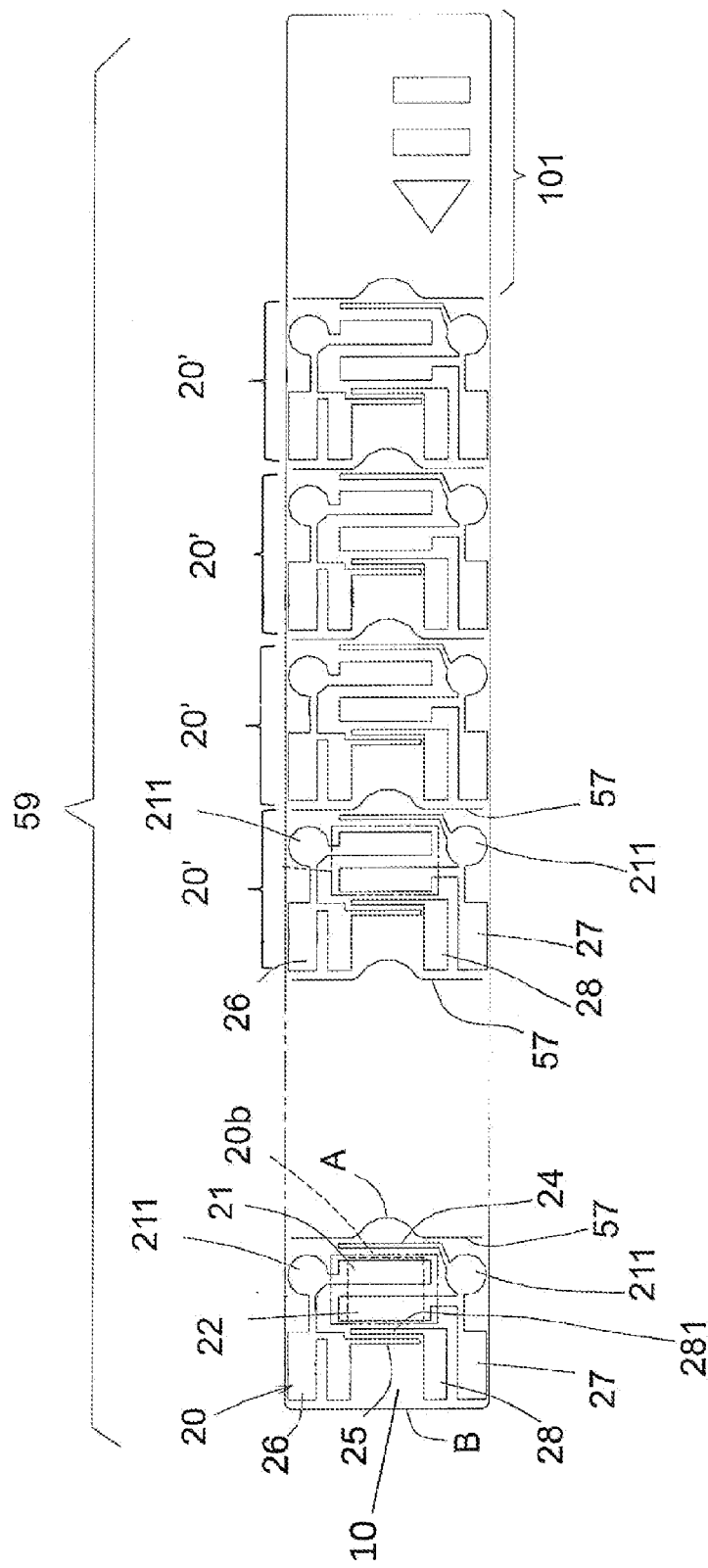
FIG. 21 shows a 2D schematic drawing of the present invention.
Figure 22:
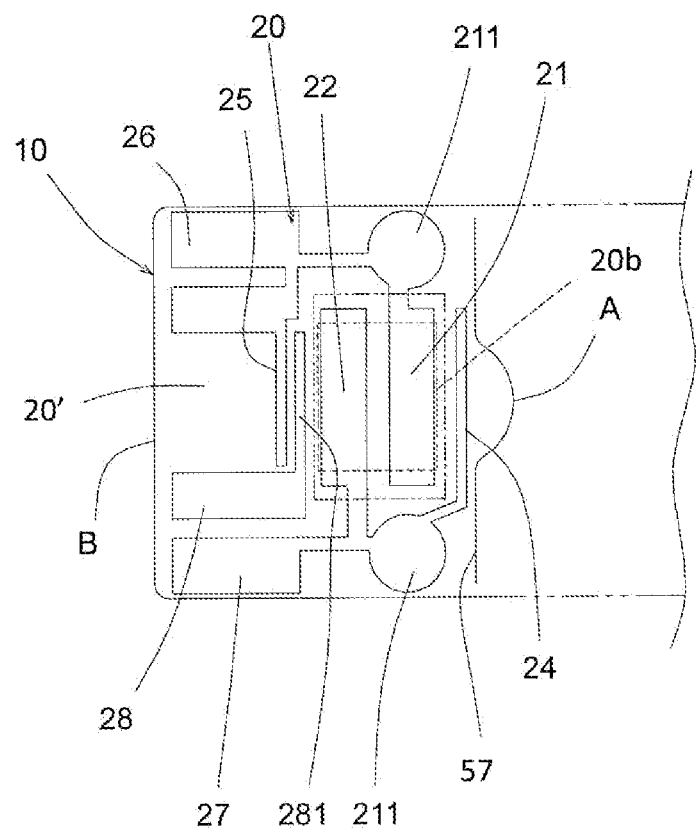
FIG. 22 shows a partially enlarged view for FIG. 21.

In a biosensor test strip (59) disclosed in the present invention, the size of the venting path (313) of the spacer layer (30) gets smaller from the front end as it leaves the reaction chamber (312) toward the rear end of the spacer layer (30). The venting path (313) passes the sensor segment (281) and the sub-working electrode (25). Since the size of the venting path (313) can be about (but not limited to) 0.01-0.8 mm, an analyte with high viscosity (such as blood) cannot pass through easily and will be blocked by the venting path (313). However, if the analyte is a control solution, the analyte can easily go through and contact the sub-working electrode (25) due to its lower viscosity. Therefore, when an electrical pulse current is obtained from the sub-working electrode (25), an electrical pulse current can be used to determine whether the analyte is a control solution or blood. The structure of venting path (313) of the above spacer layer (30) is shown in FIG. 19.

Figure 5:
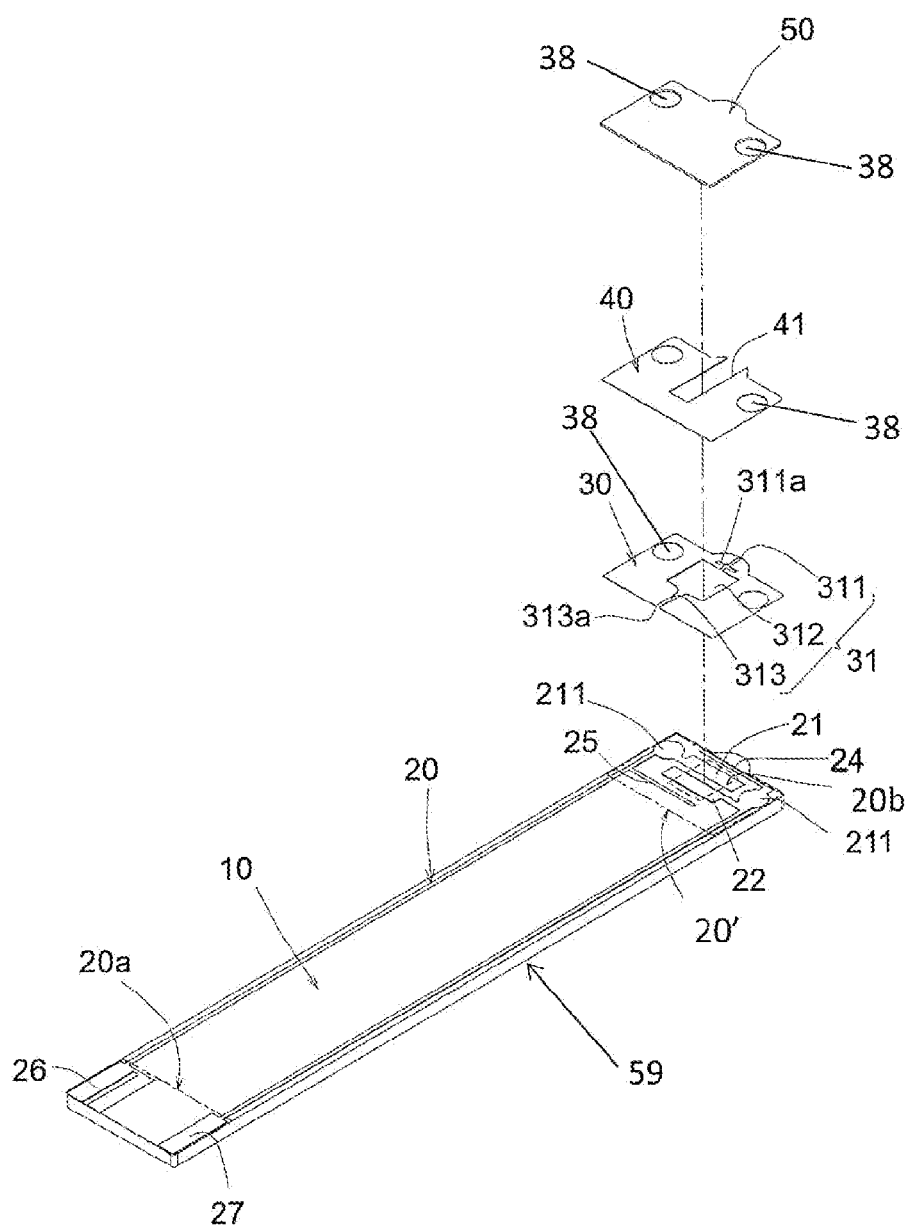
FIG. 5 shows an exploded view of the first embodiment of the present invention.
Figure 6:
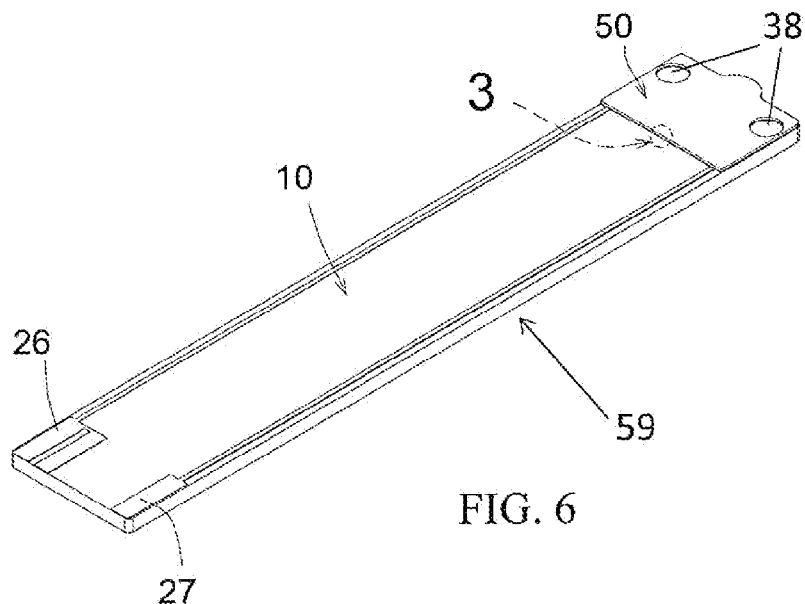
FIG. 6 shows a 3D schematic drawing of the first embodiment of FIG. 5.
Figure 7:
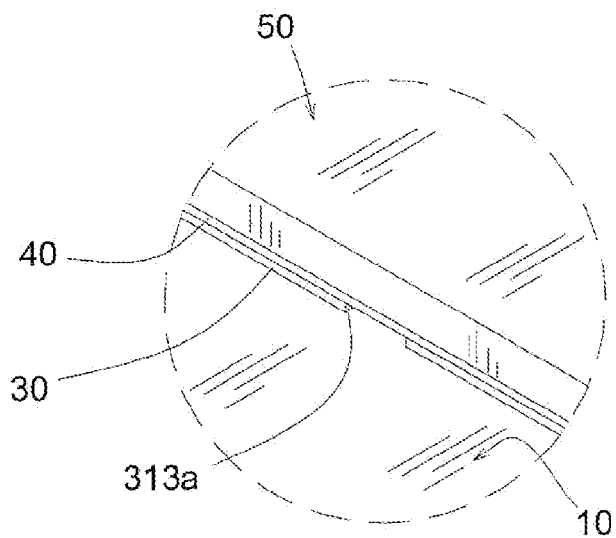
FIG. 7 shows an enlarged view of the area (3) as shown in FIG. 6.
Figure 8:
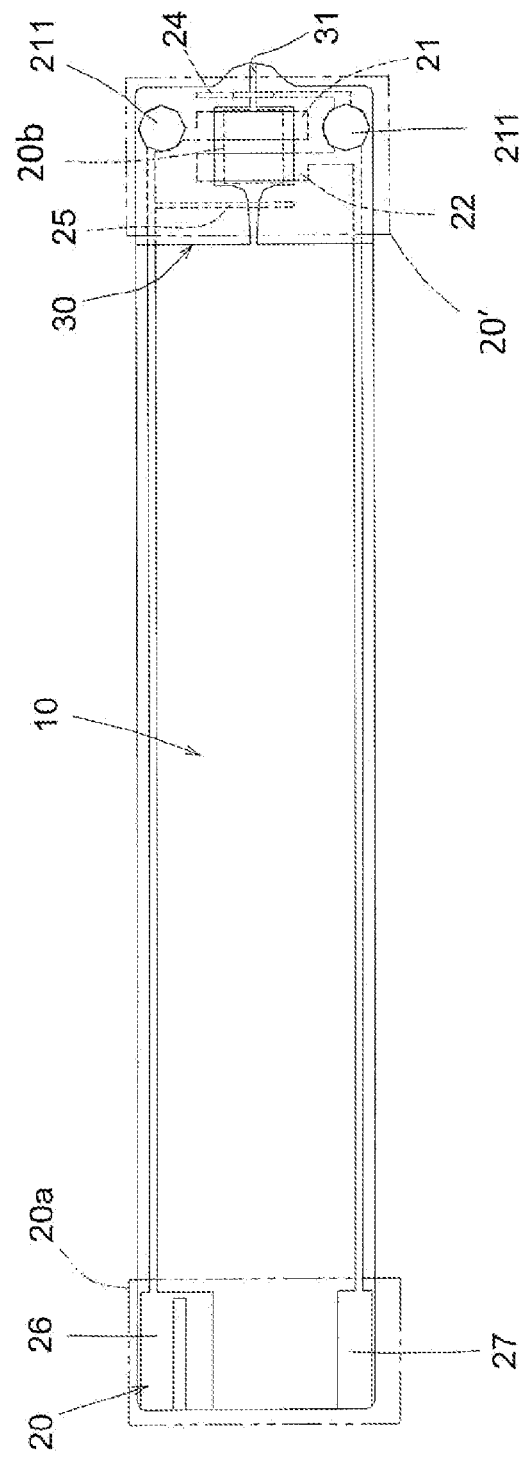
FIG. 8 shows a 2D schematic drawing for the embodiment of FIG. 5.
Figure 9:
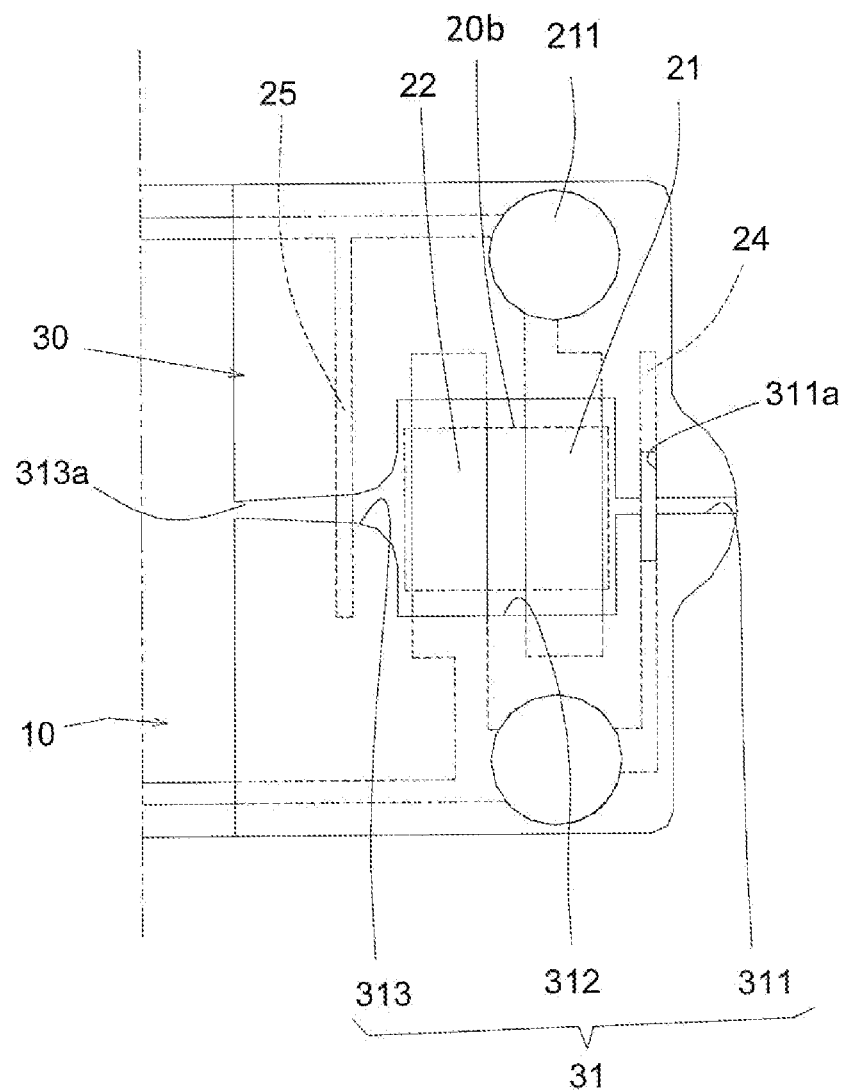
FIG. 9 shows a partially enlarged view of FIG. 8.

As shown in FIGS. 5 and 7, the air exit (313a) of the venting path (313) of the spacer layer (30) that is connected to an outer environment for air to leave which helps draw in the blood through capillary force. In addition, the air exit (313a) may be located between the substrate (10) and the adhesive layer (40). Therefore, the analyte can easily flow into the flow path (31). Moreover, the venting path (313) of the present invention can be connected to the venting hole (60), shown in other figures, which passes between the cover layer (50), adhesive layer (40), and, or, substrate (10).

The adhesive layer disclosed in the present invention may be a double sided adhesive layer, glue, etc. Alternatively, the adhesive layer (40) may be attached to the cover layer (50), the spacer layer (30) and the substrate (10) by high frequency induction heating. The adhesive layer a recess (41) for the analyte to flow through with the aid of capillary force, as well as two aperture holes (38) which corresponds to the check pads (211). The adhesive may also contain a venting hole (60) for air to leave as blood or analyte is drawn into the biosensor test strip (59).

The cover layer (50) disclosed in the present invention may be a hydrophilic PET plastic sheet, which is hydrophilic. Therefore, an analyte can easily flow under the cover layer. The cover layer (50) also houses two aperture holes (38) which corresponds to the check pads (211).

Figure 16:
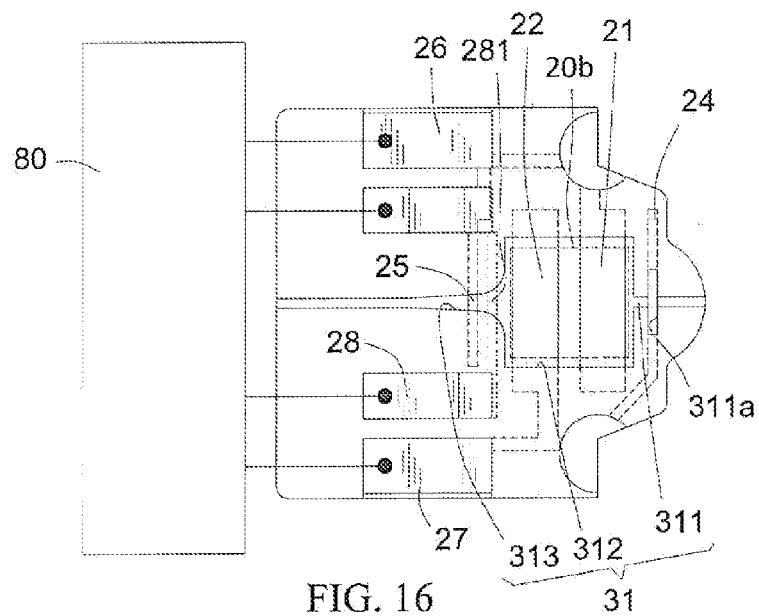
FIG. 16 shows a schematic drawing for the relationship between the embodiment shown in FIG. 12 and the biosensor monitor after a piece of the biosensor test strip is separated from the others.

As shown in FIGS. 12-16, a biosensor test strip (59) disclosed in the present invention includes a substrate (10), a conductive layer (20), a spacer layer (30), an adhesive layer (40), a cover layer (50), and a plurality of incisions (57) formed between the test sections (20'). The conductive layer (20) is on the substrate (10) and has a plurality of test sections (20'). Each of the test sections (20') has contact pads (20a), check pads (211) and a reaction zone (20b). The spacer layer (30) surrounds the reaction zone (20b) of each test section (20') of the conductive layer (20) rather than the contact pads (20a) and has a pair of aperture holes (38) corresponding to the check pads (211) on the conductive layer (20), and a plurality of flow paths (31). Each of the flow paths (31) passes through the front flow path (311), the reaction zone (20b), and the venting path (313). The adhesive layer (40) covers the spacer layer (30) without covering the contact pads (20a) of the conductive layer (20) and has a pair of aperture holes (38) corresponding to the check pads (211) on the conductive layer (20), and a recess (41) corresponding to the flow path (31). The cover layer (50) covers the adhesive layer (40) without covering the contact pads (20a) of the conductive layer (20). Therefore, each test section (20') defined by two incisions (57) forms a small piece of biosensor test strip and can be independently used on a biosensor monitor (80) as shown in FIG. 16. In addition, the contact pads (20a) contain a first contact pad (26) and a second contact pad (27). The reaction zone (20b) has a working electrode (21) and a reference electrode (22). Furthermore, the working electrode (21) is connected to the first contact pad (26). Whilst, the reference electrode (22) is connected to the second contact pad (27). The working electrode (21), the reference electrode (22) and an in-between zone form a reaction zone (20b) where reaction reagent applies. Moreover, the reaction zone (20b) has at least one additional sub-reference electrode (24) and at least one additional sub-working electrode (25). The sub-reference electrode (24) is connected to the second contact pad (27) and is located in front of the reaction zone (20b). Thus, a first electrical pulse current for defining an initial time when an analyte is applied to the biosensor test strip is obtained when the analyte contacts across the sub-reference electrode (24) and the working electrode (21). The sub-working electrode (25) is connected to the first contact pad (26) and is located in the rear end of the reaction zone (20b). Thus, a second electrical pulse current is obtained when the analyte contacts across the sub-working electrode (25) and the sub-reference electrode (24). From the first and second electrical pulse currents, the time interval for the analyte flowing through the reaction zone (20b) is defined. The fluid velocity and hence the viscosity of the analyte, which corresponds to control solution, or blood with certain Hct content, can be subsequently determined. However, if the second electrical pulse current is not received, it will be an indication that that applied analyte is not sufficient for the measurement.

Figure 17:
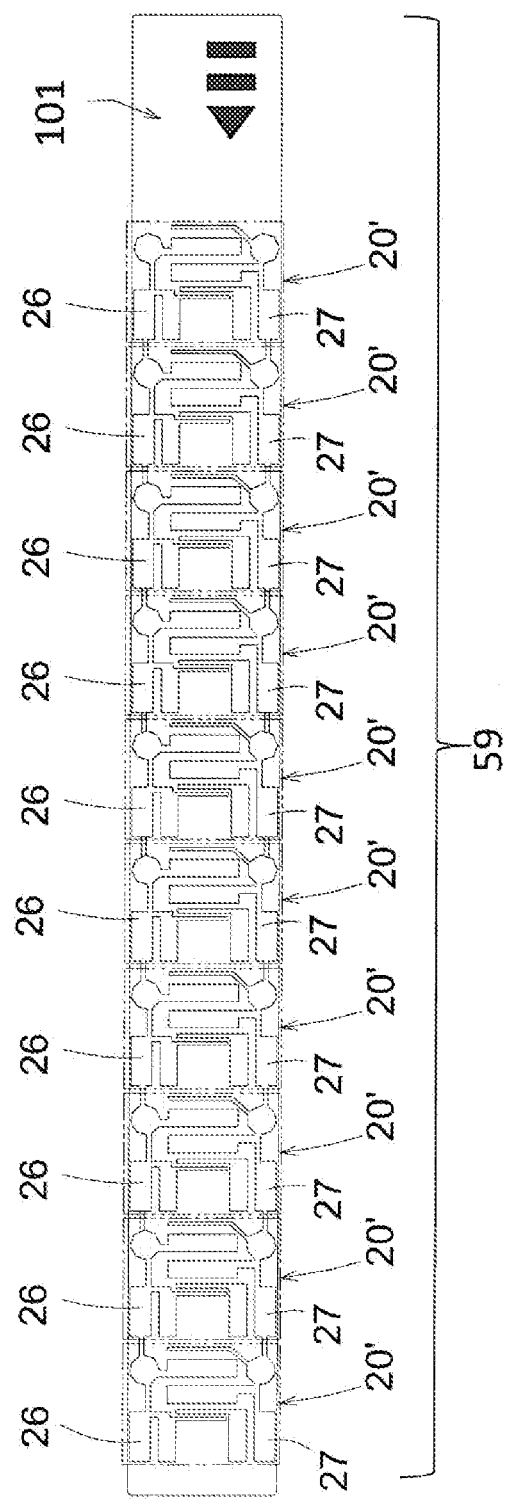
FIG. 17 shows a 2D schematic drawing of the fourth embodiment of the present invention.

As shown in FIG. 17, the test sections (20') of the conductive layer (20) are so arranged that all of the first contact pads (26), check pads (211), and working electrode (21) in the test sections (20') are electrically connected to each other. After a conductive layer (20) is formed on a substrate (10), the substrate (10) is immersed under conductive chemical solutions. Furthermore, the conductive layer (20) is connected to a positive electrode (or a negative electrode) and the conductive chemical solutions are connected to the other electrode. After an electric potential is applied, impurities on the conductive layer (20) can be removed by electrolysis. That is, the residual impurities or oxidants on the conductive tracks, working and reference electrodes, and contact pads of the conductive layer (20) can be removed by oxidation or reduction process. As a result, the stability of the biosensor test strip (59) is enhanced. After the above process, a spacer layer (30), an adhesive layer (40), a cover layer (50) with incisions (57) can be subsequently attached onto. Furthermore, after an electric potential is applied conductive tracks, working and reference electrodes, and contact pads of the conductive layer by oxidation or reduction process.

Figure 18:
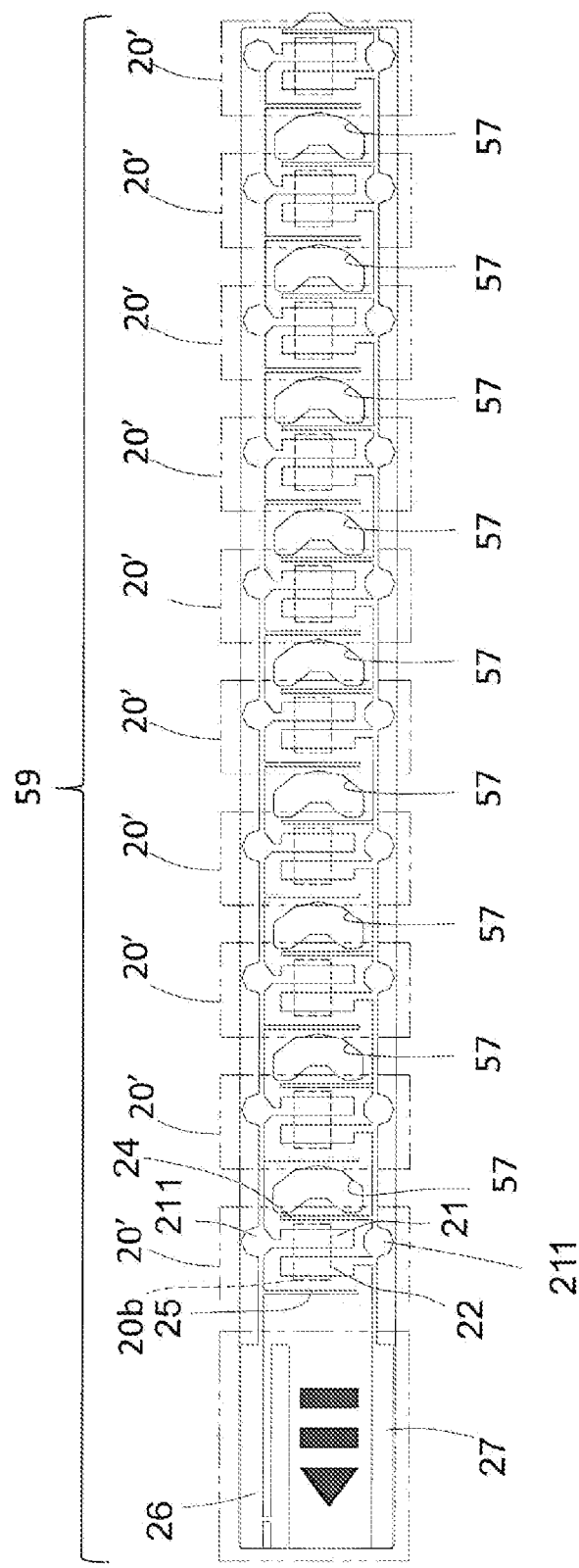
FIG. 18 shows a 2D schematic drawing of the fifth embodiment of the present invention.

As shown in FIG. 18, a biosensor test strip disclosed in the present invention includes a conductive layer (20) that has contact pads (20a), check pads (211), and a plurality of reaction zones (20b) which are electrically connected. Moreover, the contact pads (20a) have a first contact pad (26) and a second contact pad (27). Each reaction zone (20b) has a working electrode (21) and a reference electrode (22). Furthermore, the working electrode (21) is connected to the first contact pad. The reference electrode (22) is connected to the second contact pad. The working electrode (21), the reference electrode (22) and an in-between zone form a reaction zone (20b) where reaction reagent applies. Moreover, each reaction zone (20b) may contain at least one additional sub-reference electrode (24) and at least one additional sub-working electrode (25). The sub-reference electrode (24) is connected to the second contact pad (27) and is located in front of each reaction zone (20b). Thus, a first electrical pulse current for defining an initial time when an analyte is applied to the biosensor test strip is obtained when the applied analyte contacts across the sub-reference electrode (24) and the working electrode (21). The sub-working electrode (25) is connected to the first contact pad and is located behind each reaction zone (20b). Thus, a second electrical pulse current is obtained when the applied analyte contacts across the sub-working electrode (25) and the reference electrode (22). From the first and second electrical pulse currents, the time interval for the analyte flowing through the reaction zone (20b) is defined. Based on the time interval, the fluid velocity of the analyte is obtained and is used to determine if the analyte is a control solution, or blood, with Hct content of blood determined. In addition, the biosensor test strip contains a plurality of incisions (57) formed between the reaction zones (20b). Therefore, the biosensor test strip of the present invention can be used more than one test on a single strip.

In each reaction zone (20b) of the above embodiment, a working electrode (21) is connected to a first contact pad (26) and a reference electrode (22) is connected to a second contact pad (27), which are all electrically connected to the check pads (211). In addition, check pads (211) with bigger areas are close to the working electrode (21) and the reference electrode (22). During the manufacture of the biosensor test strip, quality control can be performed on such check pads (211), to see if the electrical resistance of the reaction reagent over the working electrode (21) and reference electrode (22) is within the designated range or not. Moreover, the distance between the check pads (211) and the working electrode (21) or the check pads (211) and the reference electrode (22) can be smaller than, but not limited to, 5 mm in order to put as many test sections (20') as possible on a single test strip and to enhance the accuracy of performing measurement on check pads (211).

In the biosensor test strip disclosed in the present invention, incision (57) can be a slot, an indent, a through groove etc., formed by stamping or other means. The incisions (57) can go through the cover layer (50), the adhesive layer (40), the spacer layer (30) and, or, a part of the substrate (10). Alternatively, the incisions (57) may only be formed on the cover layer (50). By applying stress on the incisions (57), a piece of biosensor test strip can be removed. The shape of the incisions (57) and the process for forming the incisions (57) are not limited.

A biosensor test strip disclosed in the present invention has the following characteristics and advantages. Its novelty and industrial utilities are obvious.

1. The test accuracy of the biosensor test strip disclosed in the present invention is enhanced because of the parameters obtained from the sub-reference electrode (24), the sub-working electrode (25) or the sensor segment (281).

2. The process of manufacturing the biosensor test strip disclosed in the present invention can be simplified because air can leave easily from the air exit (313a) of the venting path (313) of the spacer layer (30) rather than from a through hole penetrating the cover layer (50). Since the size of the venting path (313) is small, a fluid with high viscosity will be blocked. Therefore, when the applied analyte contacts the sub-working electrode (25), the type and Hct concentration of the analyte, if applicable, applied can be determined accordingly.

3. Based on the sensor segment (281), the amount of analyte can be determined to be aware of insufficient amount of analyte applied.

4. Based on the electrical pulse current provided by the contact of the analyte across the sub-reference electrode (24) and working electrode (21), the initial time when an analyte is applied can be determined. Thus, a second electrical pulse current is obtained when the applied analyte contacts across the sub-working electrode (25) and the reference electrode (22). From the first and second electrical pulse currents, the time interval for the analyte flowing through the reaction zone (20b) is used Based on the time interval, the fluid velocity of the analyte is obtained and is used to determine whether if the analyte is a control solution or blood. The Hct content of blood can be subsequently determined. However, if the second electrical pulse current is not received, it will be an indication that that applied analyte is not sufficient for the measurement.

5. In addition, the biosensor test strip contains a plurality of incisions (57) formed between the test sections (20'). Therefore, the biosensor test strip of the present invention can be used for multiple tests on a single test strip.

Figure 23:
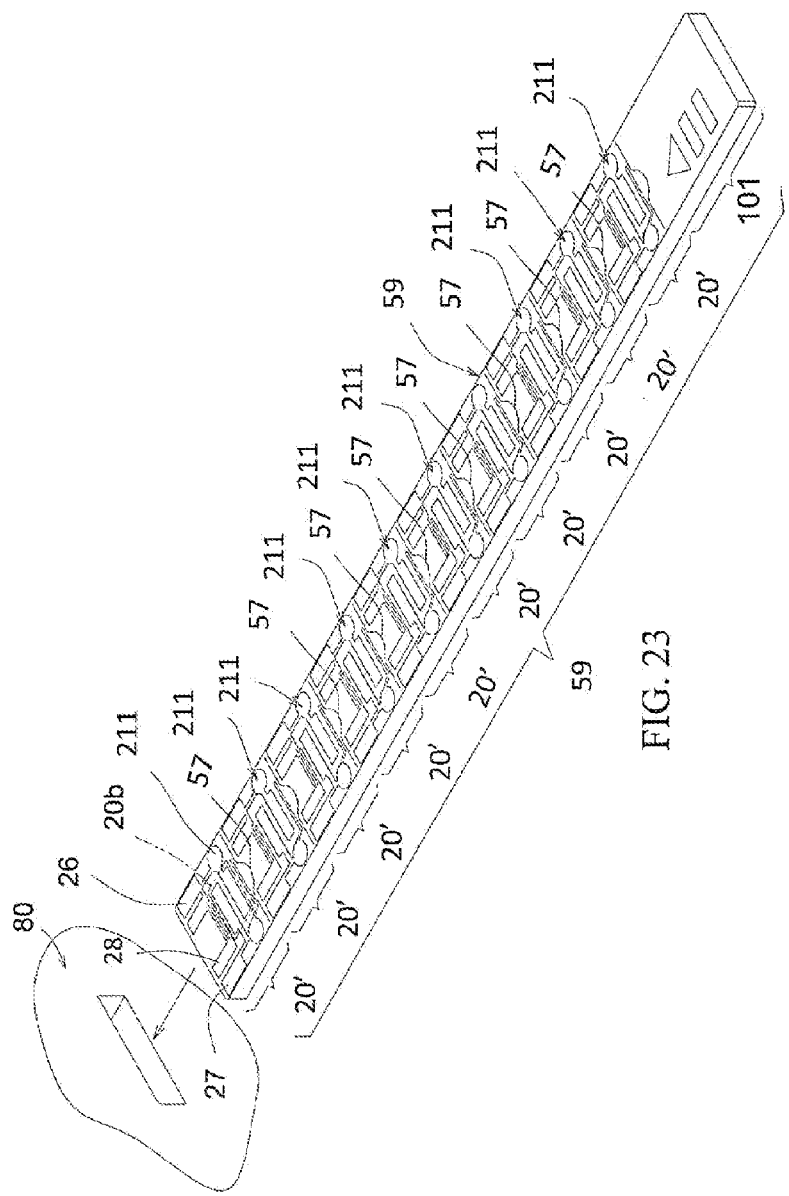
FIG. 23 shows a 3D schematic drawing to illustrate the process of the present invention being inserted into a biosensor monitor.
Figure 24:
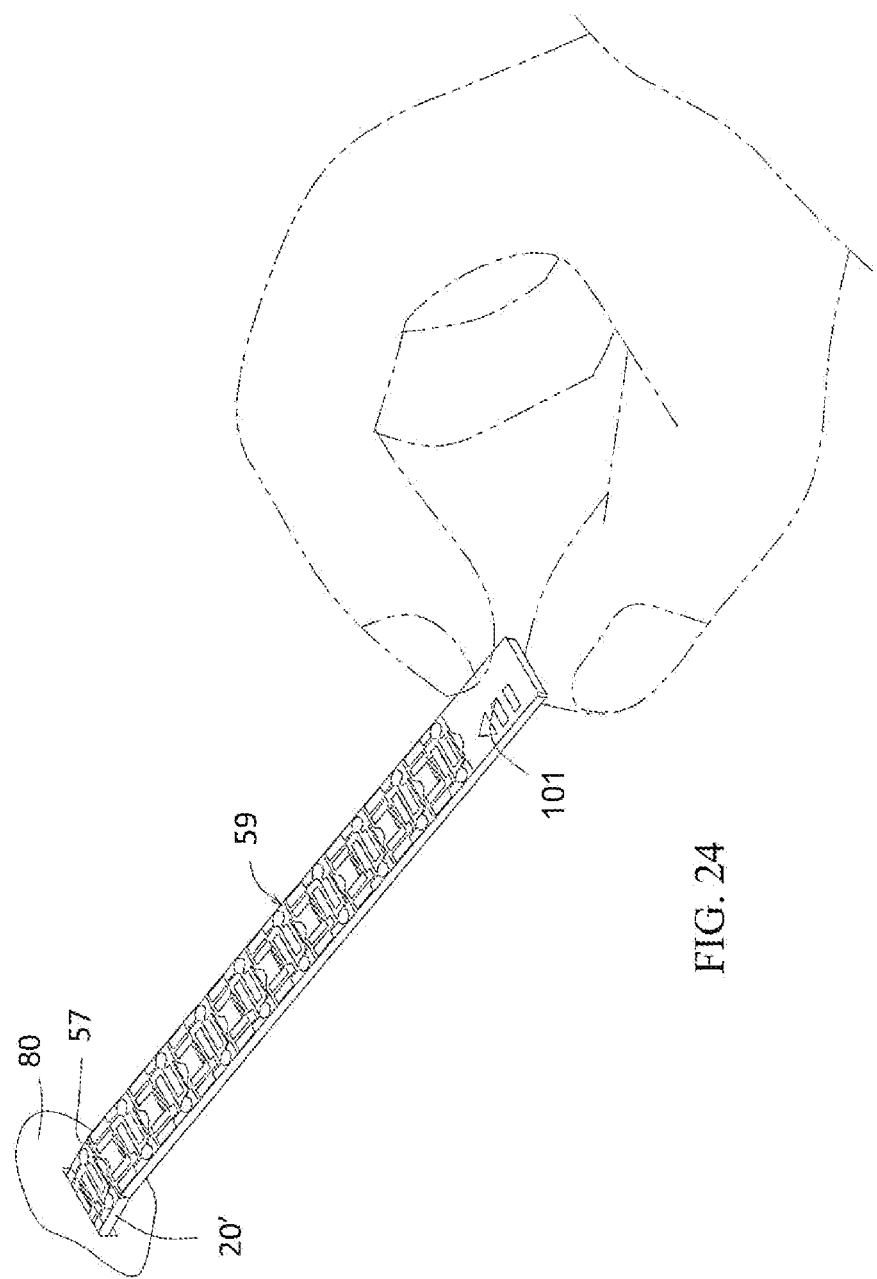
FIG. 24 shows a 3D schematic drawing to illustrate the process that a test section of the biosensor test strip of the present invention is removed from the other test sections.
Figure 25:
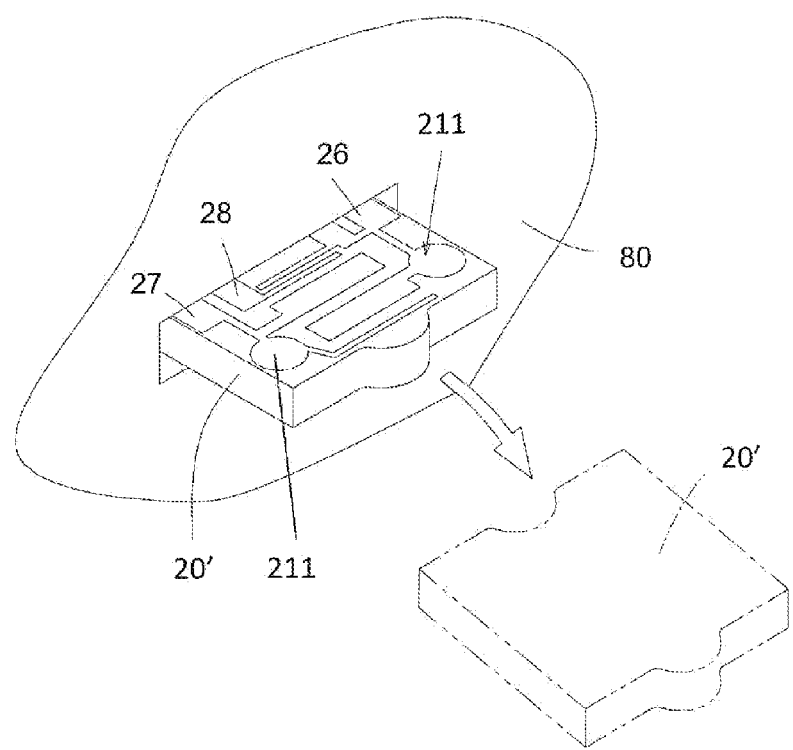
FIG. 25 shows a 3D schematic drawing to illustrate the eject process of the test section of the biosensor test strip of the present invention.
Figure 26:
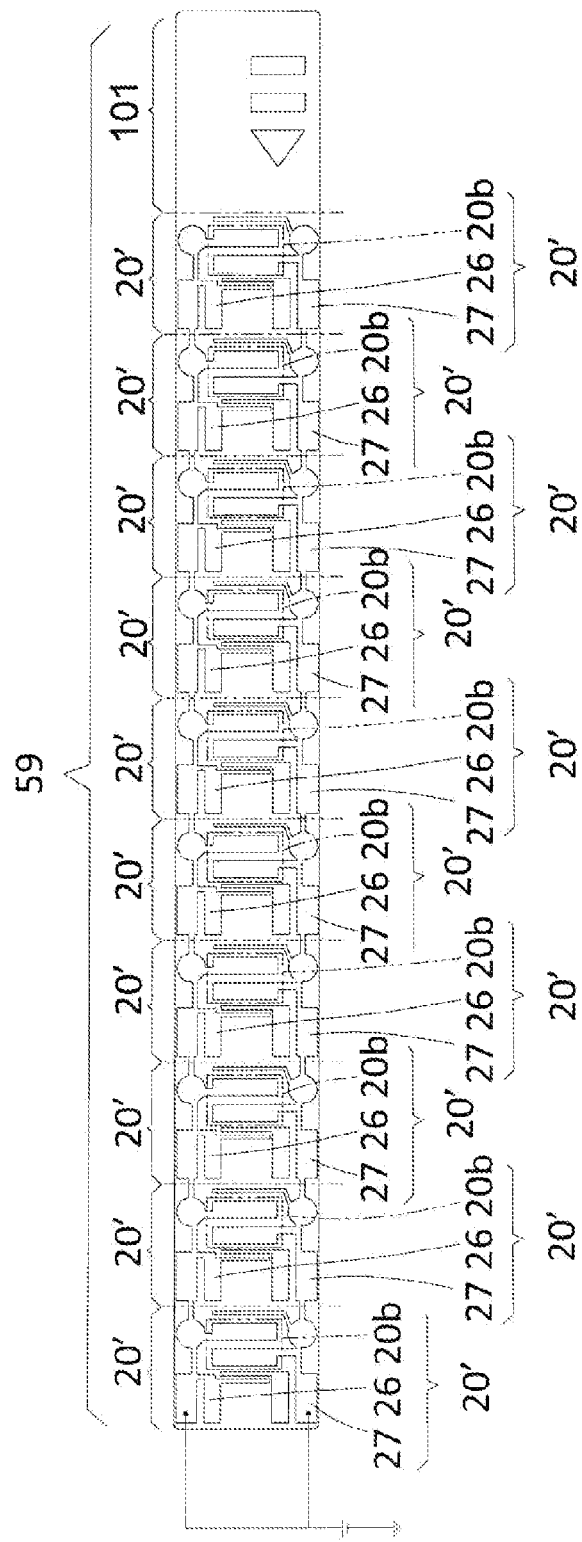
FIG. 26 shows a 2D schematic drawing for another embodiment of the present invention.

Referring to FIGS. 21-26, the present invention relates to a biosensor test strip (59) with a plurality of incisions (57) and test sections (20') that includes a substrate (10) with a plurality of incisions (57) and a plurality of conductive layers (20) on the test sections (20'). The incisions (57) can divide the substrate (10) into a plurality of test sections (20'), each of which having a first side (A) and a second side (B). The first side (A) is defined as the side away from a biosensor monitor (80) when inserting into the biosensor monitor (80). The second side (B) is defined as the side close to the biosensor monitor (80) when inserting into the biosensor monitor (80). Furthermore, each conductive layer (20) includes check pads (211), a reaction zone (20b), a first contact pad (26) and a second contact pad (27). The reaction zone (20b) is located on the first side (A) of the test section (20'). The first contact pad (26) and second contact pad (27) are electrically connected to the reaction zone (20b) and are located on the second side (B) of the test section (20'). Therefore, in use, the first test section (20') of the biosensor test strip is inserted into a biosensor monitor (80) as shown in FIG. 23 and is removed from the other test sections (20') by an incision (57) as shown in FIG. 24. As shown in FIG. 25, after the test is finished, used the test section (20') is ejected from the biosensor monitor (80) by an eject mechanism (not shown) of the biosensor monitor (80) to avoid contact with applied blood.

A biosensor test strip with a plurality of incisions (57) and test sections (20') disclosed in the present invention contains a holder (101) without any conductive layer (20) on the surface, so that a user can hold the device of the present invention by the holder (101).

In a biosensor test strip with a plurality of incisions (57) and test sections (20') disclosed in the present invention, each reaction zone (20b) includes at least one working electrode (21) and one reference electrode (22). The working electrode (21), the reference electrode (22) and an in-between zone form a reaction zone (20b) where reaction reagent applies. The working electrode (21) is connected to a first contact pad (26) and the reference electrode (22) is connected to a second contact pad (27).

In a biosensor test strip with a plurality of incisions (57) and test sections (20') disclosed in the present invention, a first contact pad (26) is connected to at least one sub-working electrode (25) and a second contact pad (27) is connected to at least one sub-reference electrode (24). A combination of several electrical pulse currents can be obtained from the sub-reference electrode (24), the working electrode (21), the reference electrode (22) and the sub-working electrode (25) once an analyte enters the biosensor test strip (59). The initial time when the analyte is applied to the biosensor test strip can be easily defined. Whenever the analyte leaves the reaction zone (20b), The time interval that the analyte flows through the reaction zone (20b) can thus be measured to determine the type and condition of the analyte applied. The present invention does not limit the number and shape of the sub-working electrode (25) and also does not limit the number and shape of the sub-reference electrode (24). The present invention can also be used in the conventional test strips and is not limited to the electrode design on the reaction zone (20b).

A biosensor test strip with a plurality of incisions (57) and test sections (20') disclosed in the present invention further includes a third contact pad (28) on the second side (B) of each test section (20') which is extended to form a sensor segment (281) between a reaction zone (20b) and a sub-working electrode (25). The third contact pad (28) and the biosensor monitor (80) are electrically connected to determine the electrical pulse current generated from the sensor segment (281) as the analyte has a viscosity so low to reach the sensor segment (282). The number and shape of the third contact pad (28) are not limited in the present invention.

In a biosensor test strip with a plurality of incisions (57) and test sections (20') disclosed in the present invention, there are check pads (211) connecting to the first contact pad (26) and the second check pads (211) respectively across the reaction zone (20b) to determine if the electrical resistance of the reaction reagent over the reaction zone is within the designated range during the manufacture of the biosensor test strip. If, however, electrical resistance of the reaction reagent over the reaction zone is outside the designated range, the biosensor test strip (59) will be marked and later removed from the batch.

In a biosensor test strip with a plurality of incisions (57) disclosed in the present invention, conductive layers (20) are arranged, such that first contact pads (26) of all the test sections (20') are electrically connected to each other and second contact pads (27) are electrically connected to each other. After the conductive layers (20) are formed on a substrate (10), the substrate (10) is immersed in conductive chemical solutions. Furthermore, the conductive layer (20) is connected to a positive electrode (or a negative electrode) and the conductive chemical solution is connected to the other electrode. After an electric potential is applied, the impurities or oxidants on the conductive layers (20) will be removed by oxidation or reduction process. As a result, the stability of the biosensor test strip is thereby enhanced. After the above process, a spacer layer (30), a hydrophilic layer, a cover layer and incisions (57) can be subsequently attached onto.

In a biosensor test strip with a plurality of incisions (57) and test sections (20') disclosed in the present invention, the main feature is that a biosensor test strip is divided to have a plurality of test sections, separated (20') by a plurality of incisions (57). Moreover, each test section (20') has its own conductive layer (20) which has check pads (211), a first contact pad (26) and a second contact pad (27) to connect to a biosensor monitor (80). When performing blood glucose tests, the first test section (20') of the biosensor test strip (59) disclosed in the present invention is inserted into the biosensor monitor (80) and then broken off to leave the other test sections (20') safely stored in the vial for further tests. An analyte (such as blood) is drawn into the biosensor test strip (59) to travel over the sensor segment (281) and the reaction zone (20b) on the first side (A) of the test section (20'). After the test, the used test section (20') in the biosensor monitor (80) can be ejected by an eject mechanism in the biosensor monitor (80). Therefore, during the eject process of the used test section (20'), the test section (20') with the analyte will not be touched to reduce blood contact with the user or caregiver.

Every time the biosensor test strip with a plurality of incisions (57) and test sections (20') disclosed in the present invention is used, only one test section (20') is left in the biosensor monitor (80). The other test sections (20') will be safely stored in a vial, which will not be degraded by either repeated exposure of humidity in the environment or applied electric potential. The accuracy of each test is thereby enhanced.

The invention has been described by exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A biosensor test strip, comprising
a substrate;
a conductive layer on the substrate, wherein
the conductive layer comprises contact pads, check pads and a reaction zone,
the contact pads comprises a first contact pad and a second contact pad,
the reaction zone comprises a working electrode and a reference electrode,
the working electrode is connected to the first contact pad,
the reference electrode is connected to the second contact pad,
the working electrode, the reference electrode and an in-between zone form the reaction zone to be covered by a reaction reagent,
the reaction zone has at least one additional sub-reference electrode and at least one additional sub-working electrode,
the sub-reference electrode is connected to the second contact pad and is located in a front end of the reaction zone, and
the sub-working electrode is connected to the first contact pad and is located in a rear end of the reaction zone;
a spacer layer surrounds the reaction zone of the conductive layer rather than the contact pads of the conductive layer to have a pair of aperture holes corresponding to the check pads, and the spacer layer has a flow path, wherein the flow path comprises a front flow path, a reaction chamber, and a venting path;
an adhesive layer covering the spacer layer without covering the contact pads of the conductive layer and having a pair of aperture holes corresponding to the check pads and a recess corresponding to the flow path; and
a cover layer covering the adhesive layer without covering the contact pads of the conductive layer, having a pair of aperture holes.

2. The biosensor test strip according to claim 1, wherein the conductive layer further comprises a third contact pad located in the contact pads and extended to form a sensor segment between the reference electrode and the sub-working electrode.

3. The biosensor test strip according to claim 2, wherein an electrical pulse current provided by the third contact pad is used to determine whether an amount of analyte is sufficient or not.

4. The biosensor test strip according to claim 2, wherein a first electrical pulse current between the sub-reference electrode and the working electrode is used to compare with a second electric pulse current between the sub-working electrode and the reference electrode and to determine control solution from blood with Hct content.

5. The biosensor test strip according to claim 1, wherein one side of the cover layer is hydrophilic.

6. The biosensor test strip according to claim 1, wherein the check pads comprise an expanded first check pad close to the working electrode and an expanded second check pad close to the reference electrode.

7. The biosensor test strip according to claim 1, wherein an electrical pulse current is provided from the analyte contact between the sub-reference electrode and the working electrode as an analyte is drawn into the biosensor test strip and is used to define an initial time when the analyte is applied.

8. The biosensor test strip according to claim 1, wherein another electrical pulse current is provided from the sub-working electrode and the reference electrode as an analyte is drawn into the biosensor test strip and is used to compare with the initial time when the analyte is applied to determine if the applied analyte is control solution or blood with Hct content.

9. The biosensor test strip according to claim 1, wherein the spacer layer is insulating glue or insulating paint.

10. The biosensor test strip according to claim 1, wherein the spacer layer is a hydrophilic plastic sheet.

11. The biosensor test strip according to claim 10, wherein the spacer layer is a plastic film which is adhered to the conductive layer by a double sided adhesive layer.

12. The biosensor test strip according to claim 10, wherein the spacer layer is a plastic film which is adhered to the conductive layer by high frequency induction heating.

13. The biosensor test strip according to claim 1, wherein the adhesive layer is attached to the cover layer and the spacer layer by high frequency induction heating.

14. The biosensor test strip according to claim 1, wherein the flow path is extended from a front end of the spacer layer to a back end of the spacer layer and passes through the front flow path, the reaction zone, and the venting path, the reaction chamber corresponds to the reaction reagent, and the venting path passes through the sub-working electrode of the conductive layer.

15. The biosensor test strip according to claim 14, wherein the flow path further comprises a guiding path, and the guiding path intersects with the front flow path and is located on the sub-reference electrode.

16. The biosensor test strip according to claim 14, wherein a distal end of the venting path is connected to an outer environment, and the distal end of the venting path is located between the substrate and the adhesive layer.

17. The biosensor test strip according to claim 16, wherein the size of an entrance of the venting path is greater than that of the distal end of the venting path.

18. The biosensor test strip according to claim 14, wherein the venting path of the spacer layer is connected to a venting hole, and the venting hole passes through the cover layer and the adhesive layer.

19. A biosensor test strip, comprising
a substrate;
a conductive layer on the substrate that has a plurality of test sections, wherein
each of the test sections has contact pads, check pads, and a reaction zone, the contact pads comprises a first contact pad and a second contact pad,
the check pads comprises one check pad electrically connecting to the working electrode and the first contact pad, and another check pad connecting to the reference electrode and the second contact pad,
the reaction zone comprises a working electrode and a reference electrode,
the working electrode is connected to the first contact pad,
the reference electrode is connected to the second contact pad, the working electrode, the reference electrode and an in-between zone form a reaction zone to be covered by a reaction reagent, the reaction zone has at least one additional sub-reference electrode and at least one additional sub-working electrode, the sub-reference electrode is connected to the second contact pad and is located in a front end of the reaction zone, and the sub-working electrode is connected to the first contact pad and is located in a rear end of the reaction zone;

a spacer layer covering the reaction zone of each of the test sections of the conductive layer rather than the contact pads and having a pair of aperture holes corresponding to the check pads, and the spacer layer having a plurality of flow paths, wherein each of the flow paths comprises a front flow path and a venting path, and passes through the front flow path, a corresponding reaction zone, and the venting path;

an adhesive layer covering the spacer layer without covering the contact pads of the conductive layer and having a pair of aperture holes corresponding to the check pads and a recess corresponding to the flow path;

a cover layer covering the adhesive layer without covering the contact pads of the conductive layer, having a pair of aperture holes corresponding to the check pads; and a plurality of incisions formed between the test sections on all substrate, spacer layer, adhesive layer and cover layer.

20. The biosensor test strip according to claim 19, wherein the test sections of the conductive layer are so arranged that the first contact pads in the test sections are electrically connected to each other and the second contact pads in the test sections are electrically connected to each other.

21. The biosensor test strip according to claim 19, wherein each of the test sections of the conductive layer further comprises a third contact pad which extends to form a sensor segment between the reference electrode and the sub-working electrode.

22. The biosensor test strip according to claim 21, wherein an electrical pulse current provided by the third contact pad is used to determine whether an amount of analyte is sufficient or not.

23. The biosensor test strip according to claim 21, wherein the first electrical pulse current between the sub-reference electrode and the working electrode is used to compare with the second electric pulse current between the sub-working electrode and the reference electrode and to determine control solution from blood with Hct content.

24. The biosensor test strip according to claim 19, wherein the working electrode is connected to the first contact pad, a first check pad with an expanded area is close to the working electrode, the reference electrode is connected to the second contact pad, and a second check pad with an expanded area is close to the reference electrode.

25. The biosensor test strip according to claim 19, wherein the incision is a slot, an indent or a through groove.

26. The biosensor test strip according to claim 19, wherein an electrical pulse current is provided from the analyte contact between the sub-reference electrode and the working electrode as an analyte is drawn into the biosensor test strip and is used to define an initial time when the analyte is applied.

27. The biosensor test strip according to claim 19, wherein another electrical pulse current is provided from the sub-working electrode and the reference electrode as an analyte is drawn into the biosensor test strip and is used to compare with the initial time when the analyte is applied to determine if the applied analyte is control solution or blood with Hct content.

28. The biosensor test strip according to claim 19, wherein the spacer layer is insulating glue or insulating paint.

29. The biosensor test strip according to claim 19, wherein the spacer layer is a hydrophilic plastic sheet.

30. The biosensor test strip according to claim 29, wherein the spacer layer is a plastic film which is adhered to the conductive layer by a double sided adhesive layer.

31. The biosensor test strip according to claim 29, wherein the spacer layer is a plastic film which is adhered to the conductive layer by high frequency induction heating.

32. The biosensor test strip according to claim 19, wherein the adhesive layer is attached to the cover layer and the spacer layer by high frequency induction heating.

33. The biosensor test strip according to claim 19, wherein the flow path of the spacer layer comprises a guiding path, the flow path is extended from a front end of the spacer layer to a back end and passes through the front flow path, the reaction zone and the venting path, a reaction chamber is formed in the flow path and corresponds to the reaction reagent, and the venting path is behind the reaction chamber and passes through the sub-working electrode and a sensor segment between the sub-working electrode and the reference electrode of the conductive layer.

34. The biosensor test strip according to claim 33, wherein the guiding path intersects with the flow path of the spacer layer and is located on the sub-reference electrode.

35. The biosensor test strip according to claim 33, wherein a distal end of the venting path is connected to an outer environment, and the distal end of the venting path is located between the substrate and the adhesive layer.

36. The biosensor test strip according to claim 33, wherein the venting path of the spacer layer is connected to a venting hole, and the venting hole passes through the cover layer and the adhesive layer.

37. The biosensor test strip according to claim 35, wherein the size of an entrance of the venting path is greater than that of the distal end of the venting path.

38. A biosensor test strip, comprising:
a substrate;
a conductive layer on the substrate that has a plurality of contact pads, check pads, and reaction zones, wherein
the contact pads comprises a first contact pad and a second contact pad,
each of the check pads comprises one check pad electrically connecting to the working electrode and the first contact pad, and another check pad connecting to the reference electrode and the second contact pad,
each of the reaction zones has a working electrode and a reference electrode,
the working electrode is connected to the first contact pad,
the reference electrode is connected to the second contact pad,
the working electrode, the reference electrode and an in-between zone form a reaction zone to be covered by a reaction reagent,
each of the reaction zones has at least one additional sub-reference electrode and at least one additional sub-working electrode, the sub-reference electrode is connected to the second contact pad and is located in a front end of the reaction zone, and the sub-working electrode is connected to the first contact pad and is located in a rear end of the reaction zone;

a spacer layer covering the reaction zones of the conductive layer rather than the contact pads of the conductive layer and having a pair of aperture holes corresponding to the check pads, and the spacer layer having a plurality of flow paths, wherein each of the flow paths has a front flow path and a venting path, and passes through the front flow path, the reaction zone and the venting path;

an adhesive layer covering the spacer layer without covering the contact pads of the conductive layer and having a pair of aperture holes corresponding to the check pads and a recess corresponding to each of the flow path;

a cover layer covering the adhesive layer without covering the contact pads of the conductive layer having a pair of aperture holes corresponding to the check pads; and a plurality of incisions formed between the test sections on the substrate, spacer layer, adhesive layer, and cover layer.

39. The biosensor test strip according to claim 38, wherein the working electrode is connected to the first contact pad, a first check pad with an expanded area is close to the working electrode, the reference electrode is connected to the second contact pad, and a second check pad with an expanded area is close to the reference electrode.

40. The biosensor test strip according to claim 38, wherein the incision is a slot, an indent or a through groove.

41. The biosensor test strip according to claim 38, wherein an electrical pulse current is provided from the analyte contact between the sub-reference electrode and the working electrode as an analyte is drawn into the biosensor test strip and is used to define an initial time when the analyte is applied.

42. The biosensor test strip according to claim 38, wherein another electrical pulse current is provided from the sub-working electrode and the reference electrode as an analyte is drawn into the biosensor test strip and is used to compare with the initial time when the analyte is applied to determine if the applied analyte is control solution or blood with Hct content.

43. The biosensor test strip according to claim 38, wherein the spacer layer is insulating glue or insulating paint.

44. The biosensor test strip according to claim 38, wherein the spacer layer is a hydrophilic plastic sheet.

45. The biosensor test strip according to claim 44, wherein the spacer layer is a plastic film which is adhered to the conductive layer by a double sided adhesive layer.

46. The biosensor test strip according to claim 44, wherein the spacer layer is a plastic film which is adhered to the conductive layer by high frequency induction heating.

47. The biosensor test strip according to claim 38, wherein the adhesive layer is attached to the cover layer and the spacer layer by high frequency induction heating.

48. The biosensor test strip according to claim 38, wherein the flow path of the spacer layer comprises a guiding path, the flow path is extended from a front end of the spacer layer to a back end and passes through the front flow path, the reaction zone and the venting path, a reaction chamber is formed in the flow path and corresponds to the reaction reagent, and the venting path is behind the reaction chamber and passes through the sub-working electrode and a sensor segment between the sub-working electrode and the reference electrode of the conductive layer.

49. The biosensor test strip according to claim 48, wherein the guiding path intersects with the flow path of the spacer layer and is located on the sub-reference electrode.

50. The biosensor test strip according to claim 48, wherein a distal end of the venting path is connected to an outer environment, and the distal end of the venting path is located between the substrate and the adhesive layer.

51. The biosensor test strip according to claim 50, wherein the size of an entrance of the venting path is greater than that of the distal end of the venting path.

52. The biosensor test strip according to claim 48, wherein the venting path of the spacer layer is connected to a venting hole, and the venting hole passes through the cover layer and the adhesive layer.

53. A biosensor test strip, comprising:

a substrate;

a conductive layer on the substrate that comprises contact pads, check pads and a reaction zone, wherein the contact pads comprise a first contact pad and a second contact pad, the check pads comprise one check pad electrically connecting to the working electrode and the first contact pad, and another check pad connecting to the reference electrode and the second contact pad, the reaction zone at least comprises a working electrode, a reference electrode, and a zone between the working electrode and the reference electrode, over which are covered by a reaction reagent;

a spacer layer covering the reaction zone of the conductive layer rather than the contact pads of the conductive layer and having a pair of aperture holes corresponding to the check pads, and the spacer layer having a flow path, wherein the flow path comprises a front flow path and a venting path, and passes through the front flow path, the reaction zone and the venting path;

an adhesive layer covering the spacer layer without covering the contact pads of the conductive layer and having a pair of aperture holes corresponding to the check pads and a recess corresponding to the flow path; and a cover layer covering the adhesive layer without covering the contact pads of the conductive layer, having a pair of aperture holes corresponding to the check pads;

the reaction chamber is located in the flow path, the venting path is located behind the reaction chamber, the size of the front flow path and the venting path are much smaller than that of the reaction chamber, and an air exit of the venting path of the flow path is connected to an outer environment and is located between the substrate and the adhesive layer.

54. The biosensor test strip according to claim 53, wherein the adhesive layer is attached to the cover layer and the spacer layer by high frequency induction heating.

55. The biosensor test strip according to claim 53, wherein a guiding path intersects with the flow path of the spacer layer.

56. The biosensor test strip according to claim 53, wherein the size of an entrance of the venting path is greater than that of the air exit.

57. A biosensor test strip, comprising:

a substrate with a plurality of incisions and test sections, wherein the incisions divide the substrate into the test sections, each of the test sections has a first side and a second side, the first side is defined as the side away from a biosensor monitor if the biosensor test strip is inserted into the biosensor monitor, and the second side is defined as the side close to the biosensor monitor if the biosensor test strip is inserted into the biosensor monitor; and a plurality of conductive layers each on a corresponding test section, wherein each of the conductive layers comprises a working electrode, a reference electrode, a sub-working electrode, a sub-reference electrode, a reaction zone, check pads, a first contact pad, and a second contact pad, wherein the check pads comprise one check pad electrically connecting to the working electrode and the first contact pad, and another check pad connecting to the reference electrode and the second contact pad, the sub-working electrode connected to the first contact pad and the sub-reference electrode connected to the second contact pad; and wherein the sub-reference electrode, the working electrode, the reference electrode, and the sub-working electrode are arranged in a direction from the first side to the second side;

the reaction zone is located on the first side of the corresponding test section, and the first and second contact pads are connected to the reaction zone and check pads and are located on the second side of the test section.

58. The biosensor test strip according to claim 57, wherein the conductive layers are so arranged that all the first contact pads are electrically connected to each other and that all the second contact pads are electrically connected to each other.

59. The biosensor test strip according to claim 57, wherein the incision formed on the substrate is a slot.

60. The biosensor test strip according to claim 57, further comprising a third contact pad which is connected to a sensor segment between the sub-working electrode and reference electrode.

61. The biosensor test strip according to claim 57, wherein a holder without any conductor layer is formed on one side of the substrate.

* * * * *